US010627386B2

(12) United States Patent
Saez et al.

(10) Patent No.: US 10,627,386 B2
(45) Date of Patent: Apr. 21, 2020

(54) SYSTEM FOR MONITORING CROPS AND SOIL CONDITIONS

(71) Applicant: Aker Technologies, Inc., Chicago, IL (US)

(72) Inventors: Orlando Saez, Chicago, IL (US); Tim Golly, Lakeville, MN (US); Todd Golly, Winnebago, MN (US)

(73) Assignee: Aker Technologies, Inc., Chicago, IL (US)

( * ) Notice: Subject to any disclaimer, the term of this patent is extended or adjusted under 35 U.S.C. 154(b) by 0 days.

(21) Appl. No.: 15/782,806

(22) Filed: Oct. 12, 2017

(65) Prior Publication Data

US 2018/0156770 A1     Jun. 7, 2018

Related U.S. Application Data

(60) Provisional application No. 62/407,299, filed on Oct. 12, 2016, provisional application No. 62/442,158, (Continued)

(51) Int. Cl.
*G01N 33/24*     (2006.01)
*G01N 33/00*     (2006.01)
(Continued)

(52) U.S. Cl.
CPC ........... *G01N 33/24* (2013.01); *A01B 79/005* (2013.01); *B64C 39/02* (2013.01); *B64C 39/024* (2013.01);
(Continued)

(58) Field of Classification Search
CPC ............... G01N 33/24; G01N 33/0098; G01N 2033/245; B64C 39/024; B64C 2201/127;
(Continued)

(56) References Cited

U.S. PATENT DOCUMENTS

| | | | |
|---|---|---|---|
| 5,435,399 A * | 7/1995 | Peterson | E02D 1/04 175/135 |
| 9,426,969 B1 * | 8/2016 | Hundt | A01K 13/006 |

(Continued)

FOREIGN PATENT DOCUMENTS

| | | |
|---|---|---|
| CA | 2973319 | 7/2016 |
| CN | 103274053 | 9/2013 |

(Continued)

OTHER PUBLICATIONS

Roland Rodriguez, "Drones will change the way agriculture works in the future," online, KRISTV.com, Aug. 11, 2016, 2 pages.

(Continued)

*Primary Examiner* — Shawn S An
(74) *Attorney, Agent, or Firm* — Barnes & Thornburg LLP

(57) ABSTRACT

According to an aspect, a system for monitoring crops and soil conditions below a crop canopy includes a retractable boom assembly adapted to be coupled to an unmanned aerial vehicle. Further according to this aspect, the boom assembly includes an actuator and an elongate probe is coupled to the retractable boom assembly. Still further, the system includes a controller for maneuvering the elongate probe below the crop canopy while the boom assembly is extended by the actuator.

24 Claims, 29 Drawing Sheets

Related U.S. Application Data filed on Jan. 4, 2017, provisional application No. 62/548,908, filed on Aug. 22, 2017.

(51) Int. Cl.

| | | |
|---|---|---|
| *B64C 39/02* | (2006.01) | |
| *A01B 79/00* | (2006.01) | |
| *B64D 47/00* | (2006.01) | |
| *G01N 33/02* | (2006.01) | |

(52) U.S. Cl.
CPC ......... *B64D 47/00* (2013.01); *G01N 33/0098* (2013.01); *G01N 33/02* (2013.01); *B64C 2201/108* (2013.01); *B64C 2201/123* (2013.01); *B64C 2201/127* (2013.01); *B64C 2201/145* (2013.01); *G01N 2033/245* (2013.01)

(58) Field of Classification Search
CPC ........ B64C 2201/108; B64C 2201/123; B64C 2201/145; A01B 79/005
See application file for complete search history.

(56) References Cited

U.S. PATENT DOCUMENTS

| | | | |
|---|---|---|---|
| 9,563,848 B1 | 2/2017 | Hunt | |
| 2002/0156556 A1* | 10/2002 | Ruffner | A01D 34/008 701/23 |
| 2006/0139037 A1 | 6/2006 | Hughes | |
| 2014/0035591 A1* | 2/2014 | Mottes | G01N 27/07 324/347 |
| 2014/0303814 A1* | 10/2014 | Burema | A01B 79/005 701/3 |
| 2014/0312165 A1 | 10/2014 | Mkrtchyan | |
| 2015/0142250 A1 | 5/2015 | Cavender-Bares et al. | |
| 2015/0321755 A1* | 11/2015 | Martin | B64C 27/50 244/17.23 |
| 2016/0050840 A1 | 2/2016 | Sauder et al. | |
| 2016/0214715 A1* | 7/2016 | Meffert | G01W 1/00 |
| 2016/0340006 A1* | 11/2016 | Tang | B63C 9/01 |
| 2016/0364989 A1* | 12/2016 | Speasl | G08G 5/0034 |
| 2017/0015416 A1* | 1/2017 | O'Connor | B64C 39/024 |
| 2017/0030877 A1 | 2/2017 | Miresmailli et al. | |
| 2017/0038749 A1 | 2/2017 | Mewes et al. | |
| 2017/0199528 A1 | 7/2017 | Detweiler et al. | |
| 2017/0223947 A1* | 8/2017 | Gall | G01N 21/4738 |
| 2017/0251589 A1 | 9/2017 | Tippery et al. | |
| 2017/0267372 A1 | 9/2017 | Donnard et al. | |
| 2017/0270616 A1 | 9/2017 | Basso | |
| 2017/0325443 A1* | 11/2017 | Crinklaw | A01M 7/0014 |
| 2018/0064049 A1 | 3/2018 | Cantrell et al. | |
| 2018/0064094 A1 | 3/2018 | Cantrell et al. | |
| 2018/0065747 A1 | 3/2018 | Cantrell et al. | |
| 2018/0065749 A1 | 3/2018 | Cantrell et al. | |
| 2018/0068164 A1 | 3/2018 | Cantrell et al. | |
| 2018/0068165 A1 | 3/2018 | Cantrell et al. | |
| 2018/0292339 A1* | 10/2018 | Gunzenhauser | A01B 79/005 |

FOREIGN PATENT DOCUMENTS

| | | |
|---|---|---|
| CN | 10597206 | 9/2016 |
| CN | 106516090 | 3/2017 |
| WO | 2016110832 | 7/2016 |
| WO | 2016123466 | 8/2016 |
| WO | 2016131007 | 8/2016 |

OTHER PUBLICATIONS

Sindhuja Sankaran et al., "Huanglongbing (Citrus Greening) Detection Using Visible, Near Infrared and Thermal Imaging Techniques," online, https://ncbi.nlm.nih.gov/pmc/articles/PMC3649375/, Feb. 6, 2013, 9 pages.

Raul Lopez-Lozano et al., "Optimal geometric configuration and algorithms for LAI indirect estimates under row canopies: The case of vineyards," online, http://www.sciencedirect.com/science/article/pii/S0168192309000550?via%3Dihub, Apr. 10, 2009, 3 pages.

Yeyin Shi et al., "Unmanned Aerial Vehicles for High-Throughout Phenotyping and Argonomic Research," online, hittp://journals.plos.org/plosone/article?id=10.1371/journal.pone.0159781, Jul. 29, 2016, 17 pages.

International Search Report and Written Opinion issued to PCT/US2017/056418, dated Jan. 17, 2018.

* cited by examiner

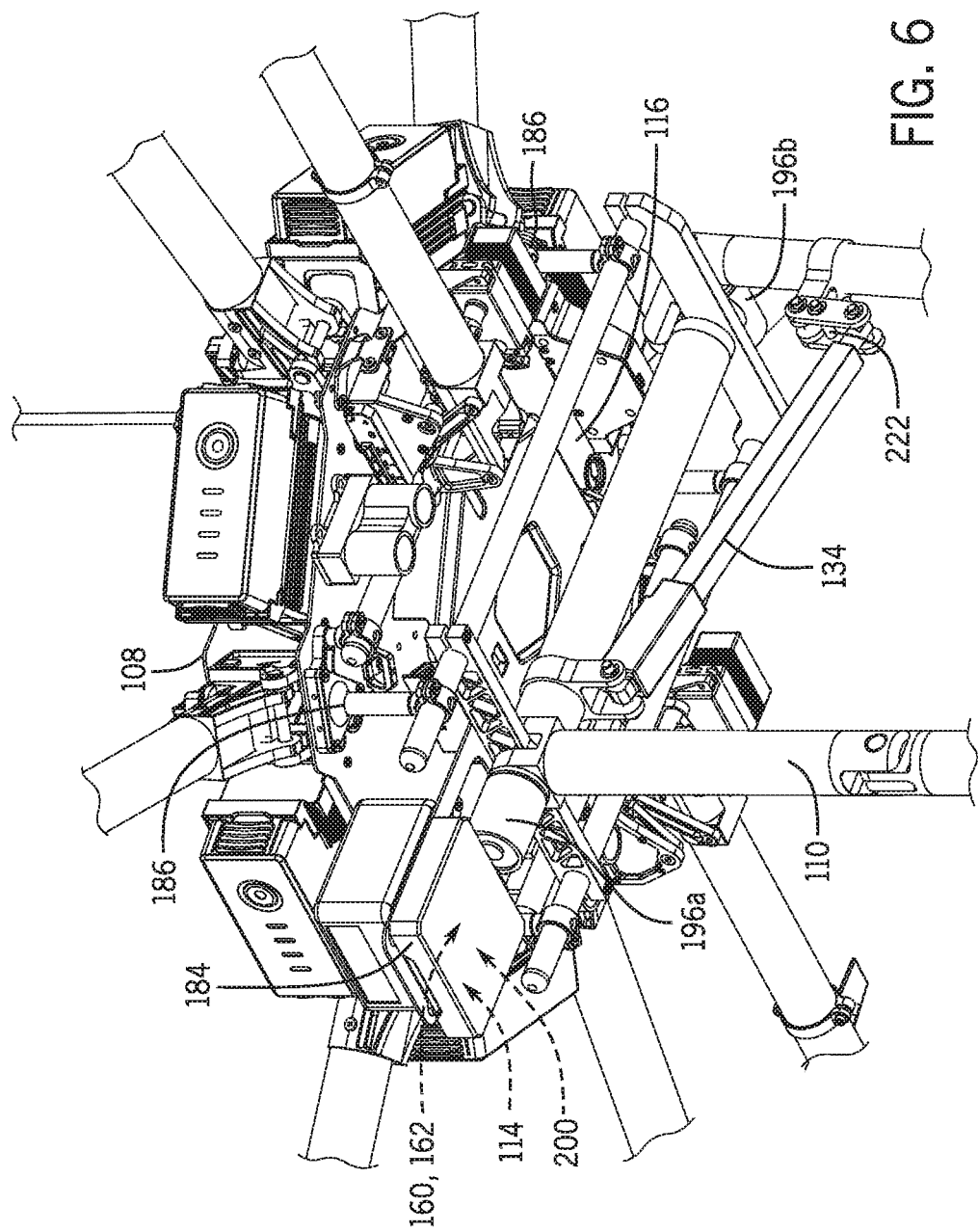

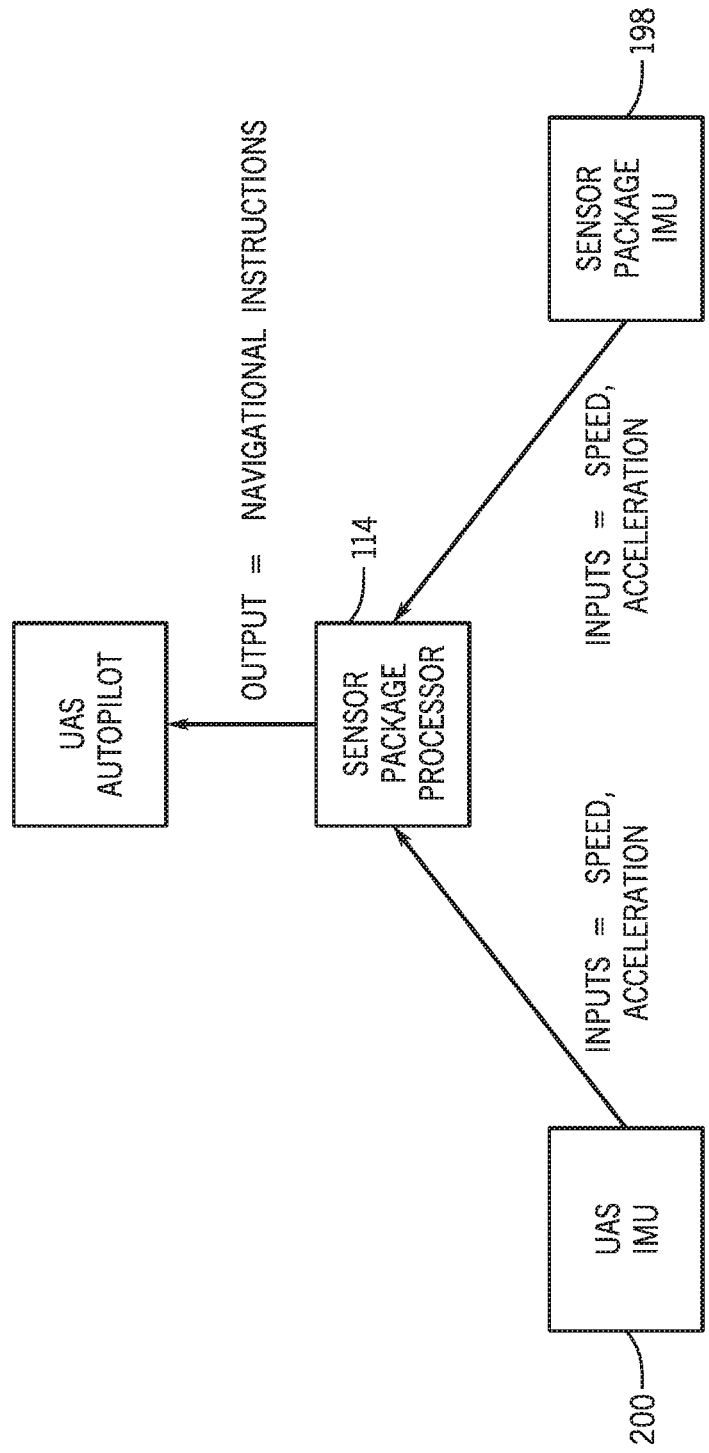

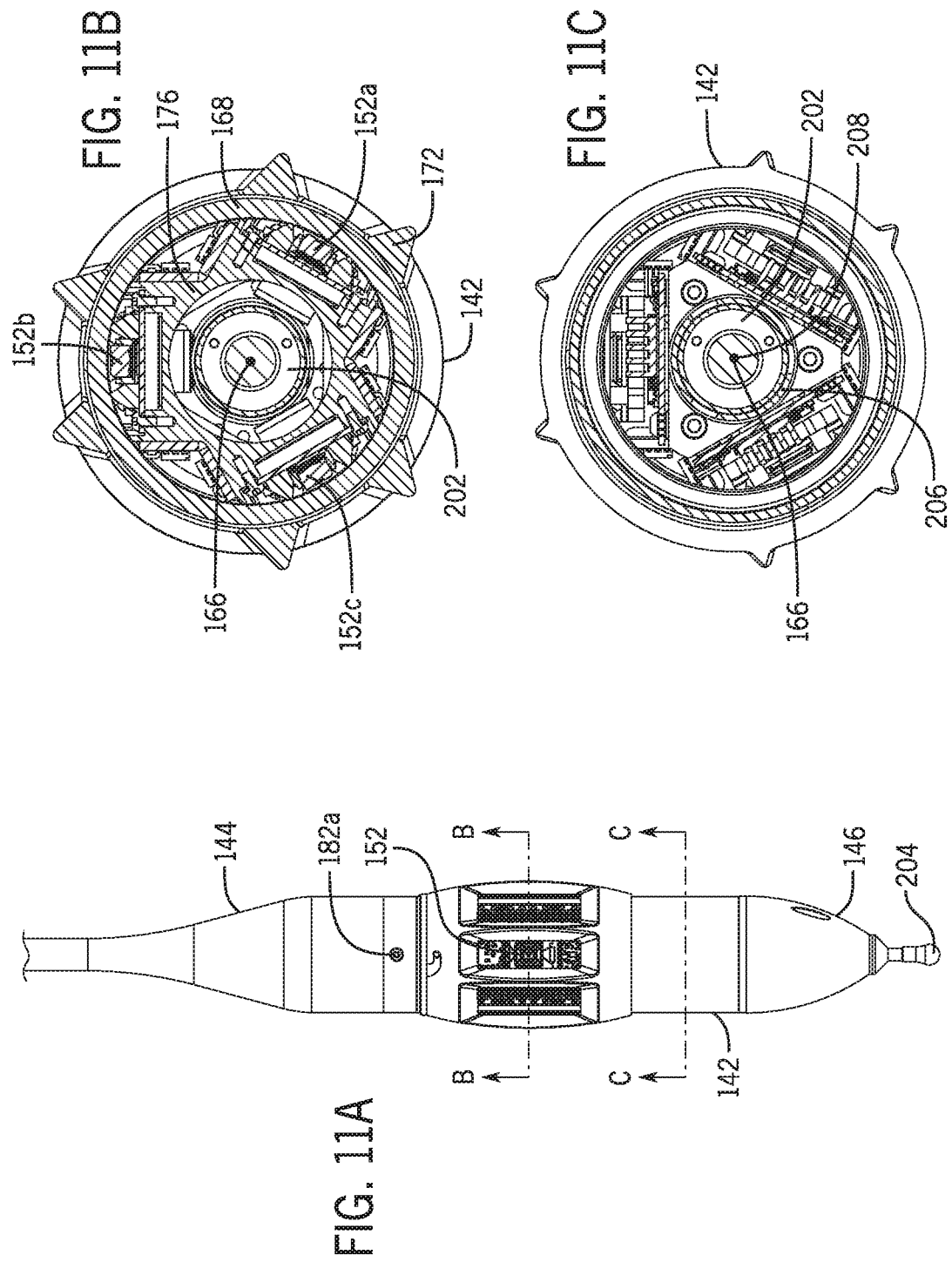

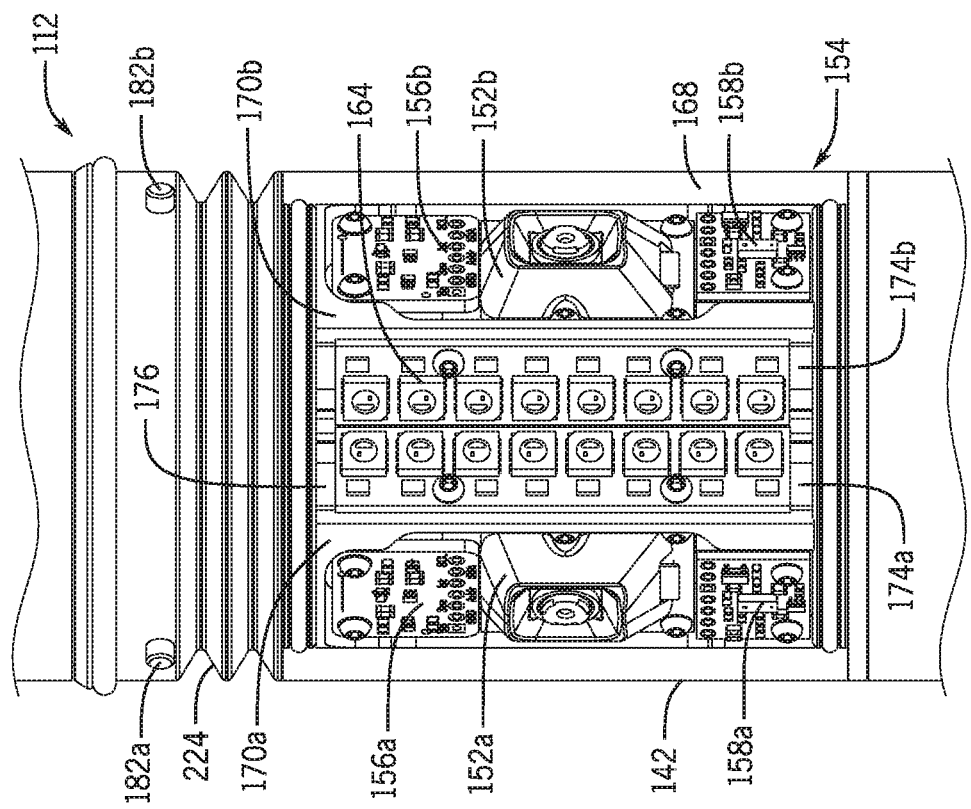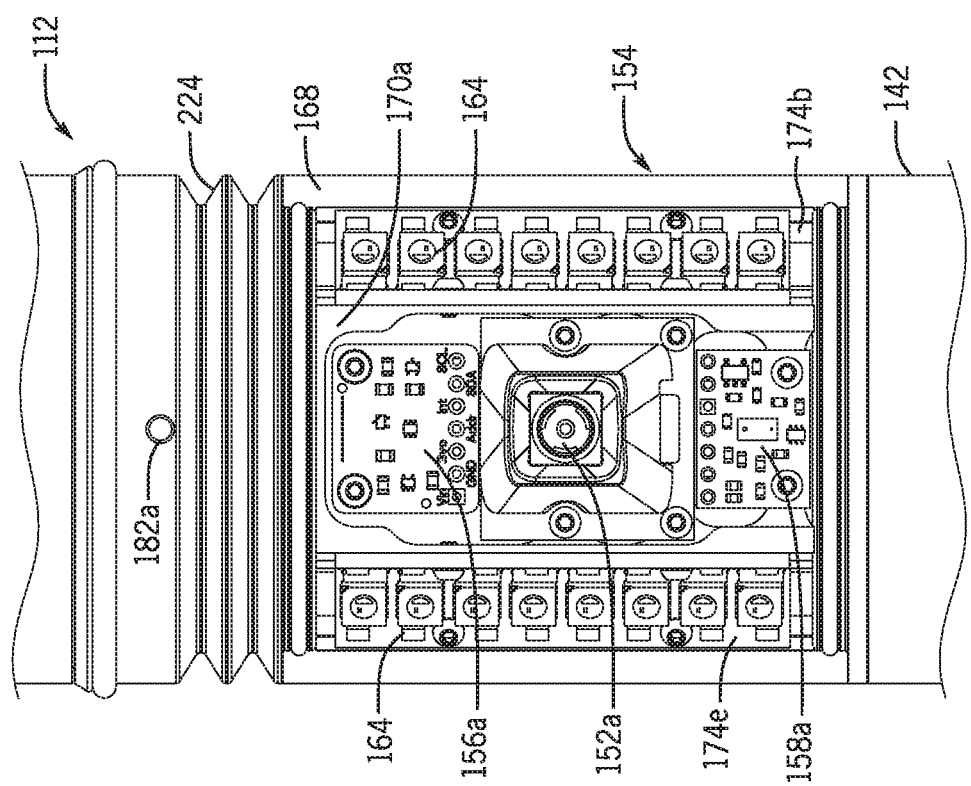
FIG. 12A
FIG. 12B

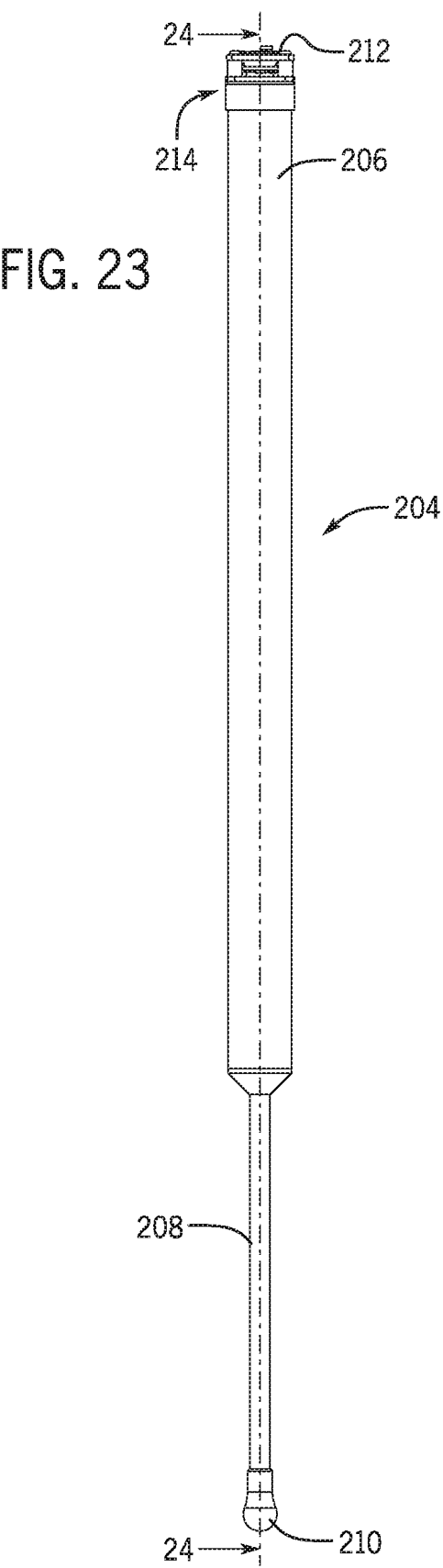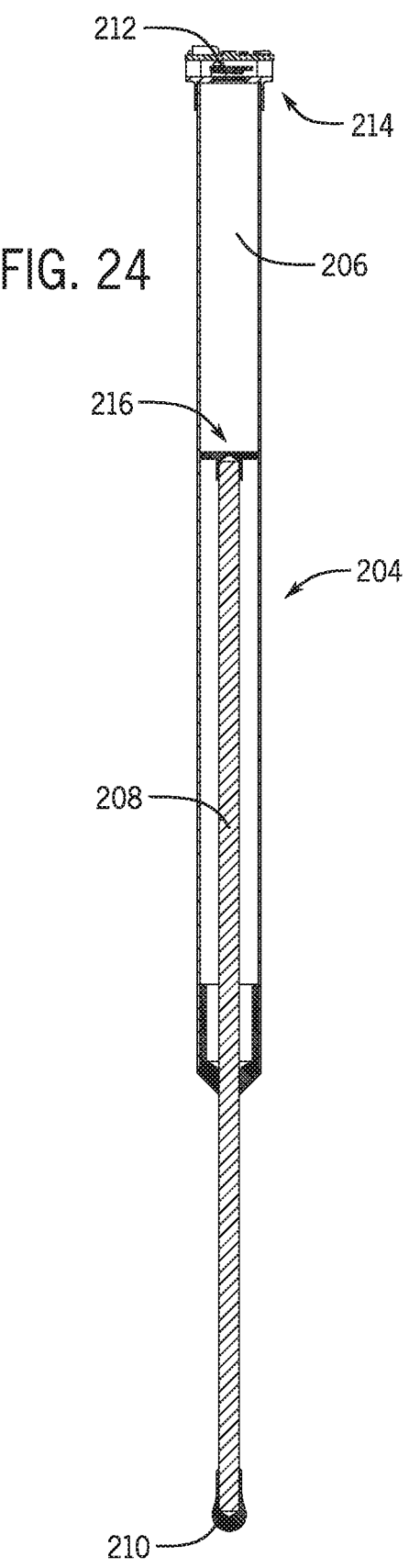

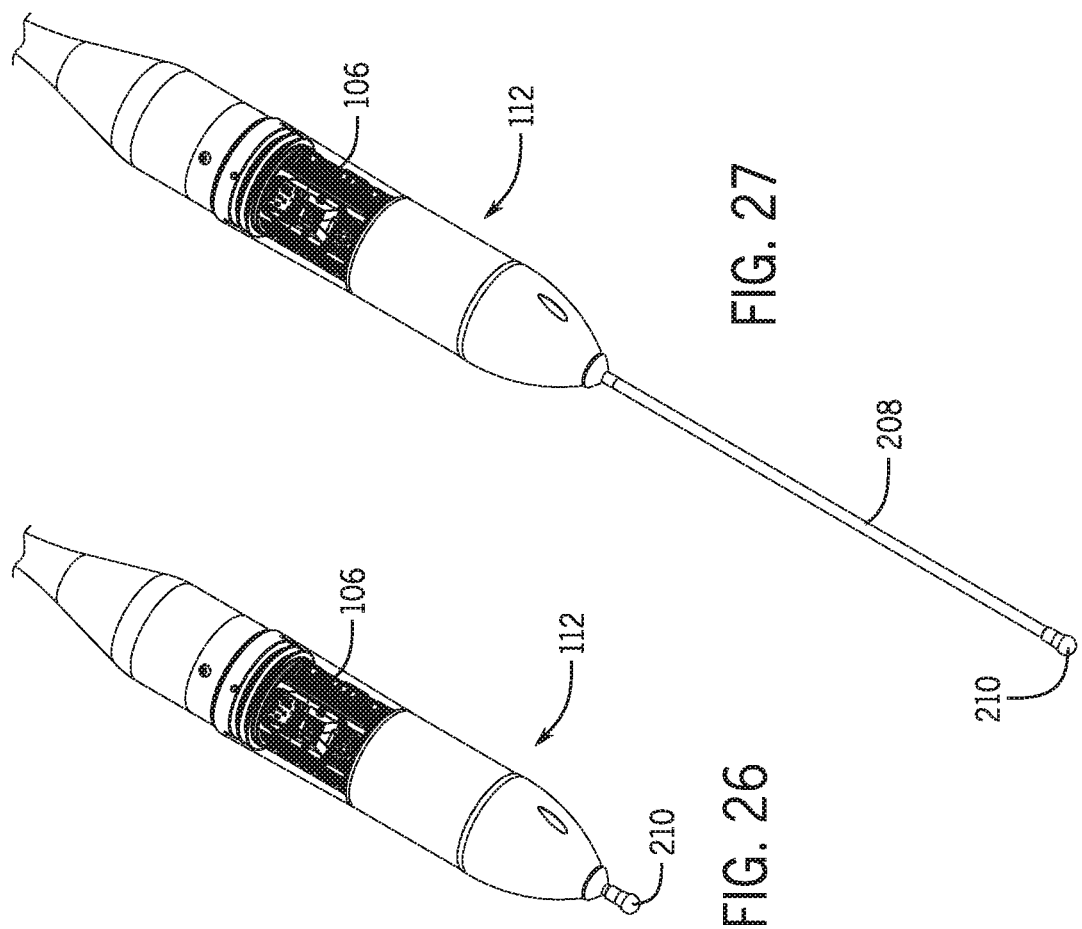
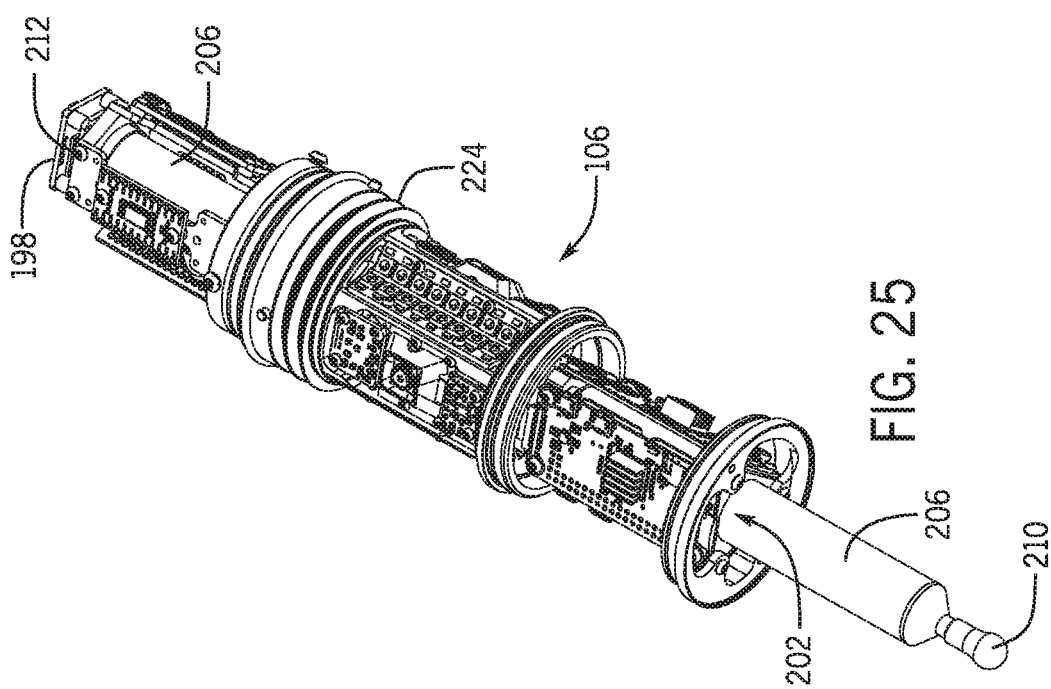

SYSTEM FOR MONITORING CROPS AND SOIL CONDITIONS

CROSS REFERENCE TO RELATED APPLICATIONS

The present application claims the benefit of U.S. provisional patent application No. 62/407,299, filed Oct. 12, 2016, entitled "Unmanned Aerial Drone Information Collection System", and further claims the benefit of U.S. provisional patent application No. 62/442,158, filed Jan. 4, 2017, entitled "Unmanned Aerial Drone Information Collection System", and further claims the benefit of U.S. provisional patent application No. 62/548,908, filed Aug. 22, 2017, entitled "System for Real-Time Assessment of Crop, Plant, and Field Conditions", all owned by the assignee of the present application and the disclosures of which are hereby incorporated by reference herein.

TECHNICAL FIELD

The present description relates in general to measurement devices, and more particularly to a probe-based system for monitoring of crop, plant and field conditions.

BACKGROUND OF THE DISCLOSURE

Each year, farmers incur substantial losses from weather, crop disease, pests, and poor field management. Growing crops at large scale creates many challenges for growers, agricultural retailers and consultants, and agricultural pesticide distributors and manufacturers. Consistent and accurate monitoring of crops is desirable across all growth stages thereof. Current methods of crop health monitoring are manually intensive, time consuming, and prone to error. However, it is difficult to properly monitor crops for insects, disease, plant nutritional deficiencies, and environmental effects due, in part, to the large size of individual fields, large scale of farm operations, and lack of available labor in the agricultural industry. Currently, in order to monitor crops, growers perform physical crop scouting during which a human walks the fields and makes manual observations of the crops. Alternatively, remote sensing methods such as satellite, manned aircraft, and/or unmanned aerial vehicles may be used to monitor crops.

Physical crop scouting does not allow for timely or high resolution monitoring simply because a human cannot efficiently cover the extent of agricultural land. Physical crop scouting may be challenging to accomplish due to the size and density of the crop (e.g. 10 foot tall corn) as well as environmental conditions such as water logged soils. Human laborers are relatively less productive in harsh climates due to heat, humidity, and other weather conditions. Random scouting (e.g., walks through the fields) may produce a small sample representation of the field, and regression modeling based thereon may establish remedial recommendations. Industry evidence suggests that random scouting often covers less than 10% of the field area while many other fields go un-sampled. Therefore, the farmer may miss early warning indications of crop loss or yield limiting factors. Similarly, remote sensing methods have associated difficulties. While remote sensing may quickly monitor large areas, it only captures the reflectance of light, standard imagery, and other sensor data available from above the crop.

Crop and vegetation observations from satellites, planes, and unmanned aerial vehicles (e.g., drones) coupled with weather and other historical field and environmental data may be used as inputs into data science prediction models that provide a probability of diagnoses. Despite significant investments in this arena, adoption of these agricultural models and implementation of actions based on predictive modeling results are relatively infrequent. Remote sensing may capture plant stress, but may not capture the true cause of crop health decline. In view of these challenges, many growers use a combination of remote sensing and physical scouting. However, implementing multiple crop monitoring methods increases the time between data collection and grower action. Timely crop monitoring is critical to minimize the effect of yield loss. To optimally preserve yield, crops should be monitored weekly, but growers may struggle to properly monitor a crop even once a growing season.

For agricultural retailers and consultants, current scouting methods limit the expansion of business and impede the service provided to growers. These retailers depend on the sale of fungicides, insecticides, and other crop protection products. However, if crop stresses are not uncovered through monitoring, crop protection products cannot be prescribed to counter yield-affecting stresses thereby decreasing potential sales for the retailers.

Further, agricultural distributors and manufacturers do not know where and when insects and diseases will affect crops across a geographic region during the growing season because there is not a timely, accurate, geo-referenced report of in-season crop stresses. Such a report is desirable in the art, and distributors and manufactures could use such information to gain efficiencies in warehousing, distribution, and sales of crop-treating products. A crop monitoring system that is timely, georeferenced, scales to large areas, and determines the cause of crop stress represents an improvement in crop monitoring practices.

The description provided in the background section should not be assumed to be prior art merely because it is mentioned in or associated with the background section. The background section may include information that describes one or more aspects of the subject technology.

SUMMARY

According to an aspect, a system for monitoring crops and soil conditions below a crop canopy includes a retractable boom assembly adapted to be coupled to an unmanned aerial vehicle. Further according to this aspect, the boom assembly includes an actuator and an elongate probe is coupled to the retractable boom assembly. Still further, the system includes a controller for maneuvering the elongate probe below the crop canopy while the boom assembly is extended by the actuator.

According to another aspect, a system for aerial monitoring and sampling of crops and soil conditions includes an unmanned aerial vehicle, a retractable boom assembly coupled to the unmanned aerial vehicle, and an elongate probe having a sensor package configured to operatively couple to the retractable boom assembly and the unmanned aerial vehicle. Also, said retractable boom assembly is coupled to an unmanned aerial vehicle, and the retractable boom assembly retracts the elongate probe during launch and landing of the unmanned aerial vehicle. Additionally, the retractable boom assembly extends the elongate probe away from the unmanned aerial vehicle during flight such that the elongate probe enters a space below a crop canopy.

According to yet another aspect, a method of monitoring crops and soil conditions includes operatively coupling a retractable boom assembly and elongate probe to an unmanned aerial system, retaining the retractable boom assembly and the elongate probe in a first position retracted proximal a body of the unmanned aerial system during launch, and extending the retractable boom assembly and the elongate probe to a second position distal the body of the unmanned aerial system during flight. Further in accordance with this aspect, the method includes dipping the elongate probe below a plant canopy while the elongate probe is in the second position, acquiring data with one or more sensors disposed in the elongate probe during the dipping maneuver, and retracting the retractable boom assembly and the elongate probe to the first position during landing.

Other aspects and advantages of the present invention will become apparent upon consideration of the following detailed description and the attached drawings wherein like numerals designate like structures throughout the specification.

BRIEF DESCRIPTION OF THE DRAWINGS

FIGS. 5 and 6 depict enlarged, isometric views from below of a lower portion of the unmanned aerial vehicle from the system of FIGS. 1A-1D, at different angles;

FIG. 9A depicts a block diagram of electronics communications within the system of FIGS. 1A-1D;

FIG. 11A is a side elevational view of the elongate probe;

FIGS. 11B and 11C are cross-sectional views of the elongate probe taken along lines B-B and C-C of FIG. 11A, respectively;

FIG. 12A is a partial, enlarged side elevational view of the elongate probe;

FIG. 12B is a partial, enlarged side elevational view of the elongate probe of FIG. 12A rotated 60 degrees;

FIG. 23 is a side elevational view of the ground contact probe of FIG. 21;

FIG. 24 is a cross-sectional view of the ground contact probe taken alone line 24-24 of FIG. 23;

FIG. 25 is a partial, enlarged, isometric view of the elongate probe with an exterior wall removed therefrom;

FIGS. 26 and 27 are isometric views of the elongate probe with the ground contact probe fully compressed and fully extended, respectively.

Figure 1B:
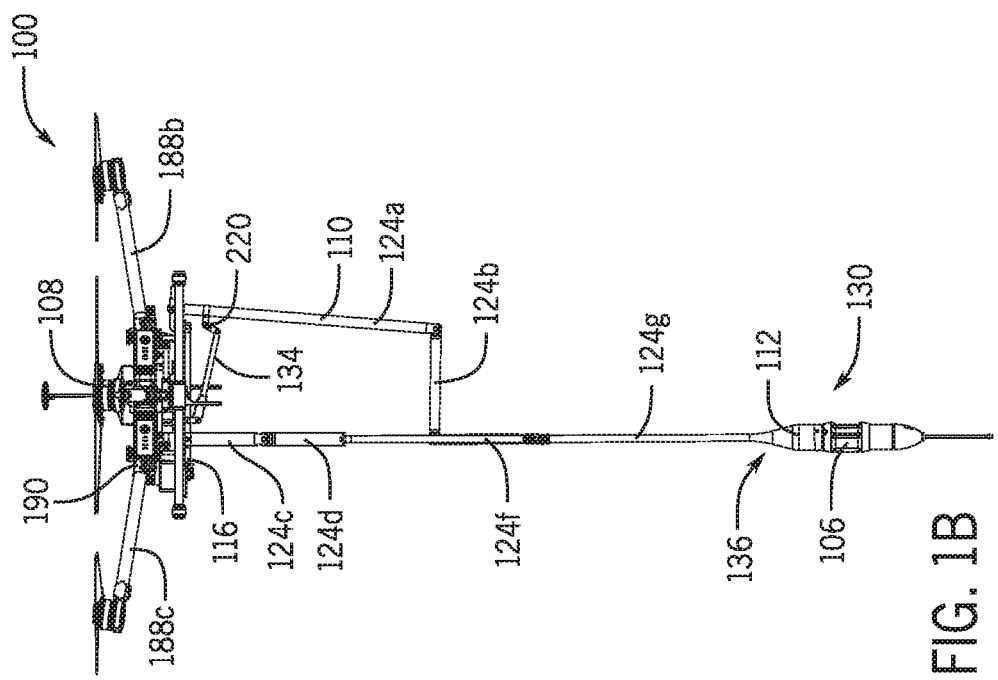
FIGS. 1A and 1B depict front and side elevational views, respectively, of a crop monitoring system including an elongate probe, retractable boom assembly, and unmanned aerial vehicle.
Figure 1A:
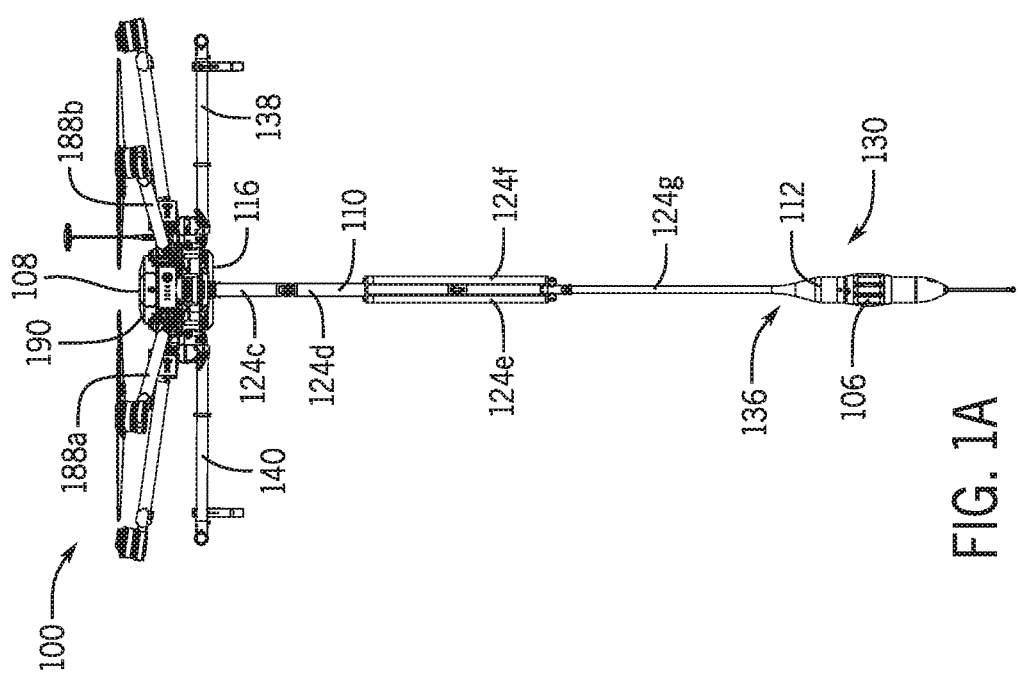
Figure 1C:
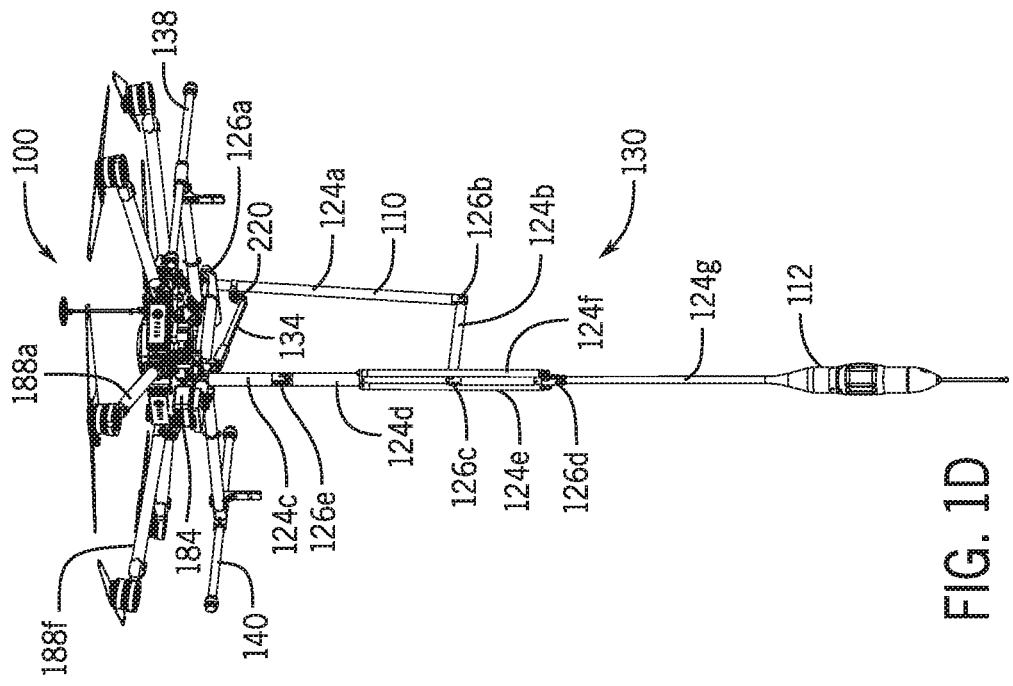
FIGS. 1C and 1D depict isometric views from below of the system of FIGS. 1A and 1B, at different angles.
Figure 1D:
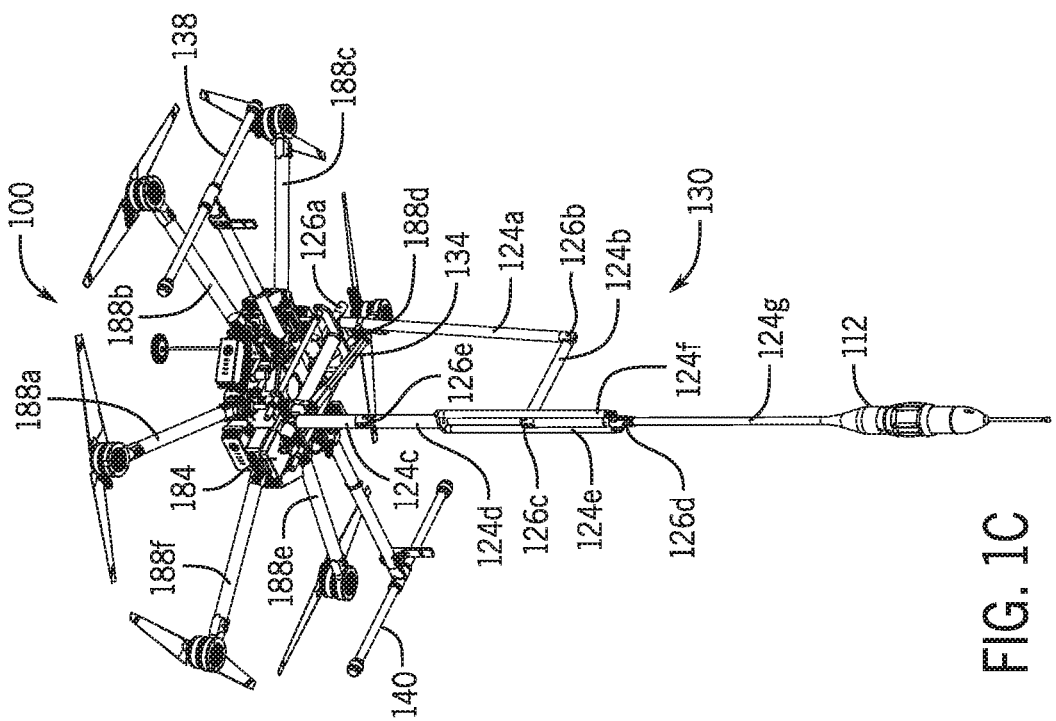

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive. Throughout this disclosure, the terms "farmer" and "grower" have the same general meaning and are used interchangeably. Similarly, the terms "crop(s)" and "plant(s)" have the same general meaning and are used interchangeably herein.

Referring to FIGS. 1 and 2, a system 100 disclosed herein allows for crop monitoring within a canopy 102 wherein the canopy 102 is the aboveground portion of one or more plant(s) or a crop 104, formed by the collection of individual plant crowns. The system 100 includes a sensor package 106 coupled to an unmanned aerial system/vehicle (UAS) 108 by a retractable arm 110. The crop monitoring system 100 includes hardware sensors and UAS flight navigation methods that operate to "dip" (See FIG. 28) the sensor package 106 below the canopy 102 of the crop to take one or more sensor readings within a space 122 below the canopy 102. The sensor package 106 thereby gathers information concerning the crop 104, understory, and ground conditions. According to some embodiments of the presently disclosed system, an elongate probe 112 carries the sensor package 106, which is used for real-time, on-site data acquisition of parameters relating to crops, plants, and field conditions. The data acquired thereby may be collected and processed by hardware sensors, software, and associated support equipment included in the crop monitoring system 100 for imaging and sampling biotic and abiotic matrices. The elongate probe 112 may be operated as a handheld device and/or portions thereof may be mounted to a host platform, such as an autonomous vehicle, manned vehicle, or stationary installation in the field.

Exemplary UAS 108 include unmanned aerial vehicles (e.g., drones, multirotor craft vehicles, and quadcopters); however, manned aerial vehicles are contemplated hereby. The UAS 108 may transport the elongate probe device 112 to target sampling locations 218 for data acquisition. Flight of the UAS 108 may be managed manually and/or based on programmed parameters. The UAS 108 and/or the elongate probe 112 may communicate with a controller, microprocessor, and/or another suitable computing device 114 (See FIGS. 6 and 9A) for control operations, transmission of data acquired, and/or processing of observed data, as applicable. The elongate probe 112 may be removably coupled to or integral with the UAS 108. The elongate probe 112 may extend from a lower portion 116 of the UAS 108 for the purpose of more easily accessing the space 122 below the canopy 102 at the target sampling locations/points 218. The elongate probe 112 may be adjustable in length and/or orientation so as to be directed as desired for a particular application.

Figure 2A:
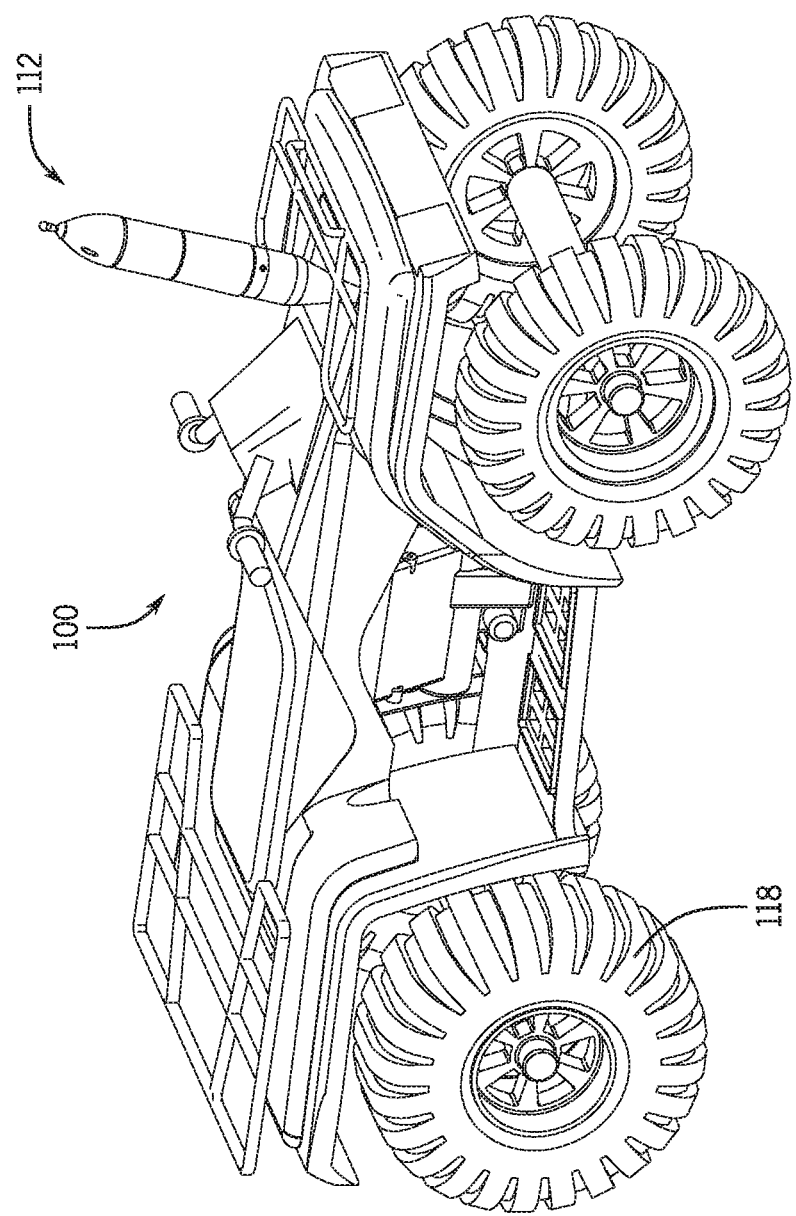
FIG. 2A depicts the elongate probe attached to a ground vehicle.

Referring now to FIG. 2A, the elongate probe 112 may be operated in concert with a ground vehicle 118 for acquiring data. Exemplary ground vehicles include manned or unmanned ground vehicles, all-terrain vehicles, motor vehicles (e.g., truck or SUV), etc. The ground vehicle 118 may transport the elongate probe 112 and sensor package 106 to target locations for data acquisition. The elongate probe 112 may be removably coupled to or integral with the ground vehicle 118. The elongate probe 112 may extend from a portion of the ground vehicle 118 to more easily access target locations. Further, the elongate probe 112 may be adjustable in length and/or orientation while mounted on and/or coupled with the ground vehicle 118.

Figure 2B:
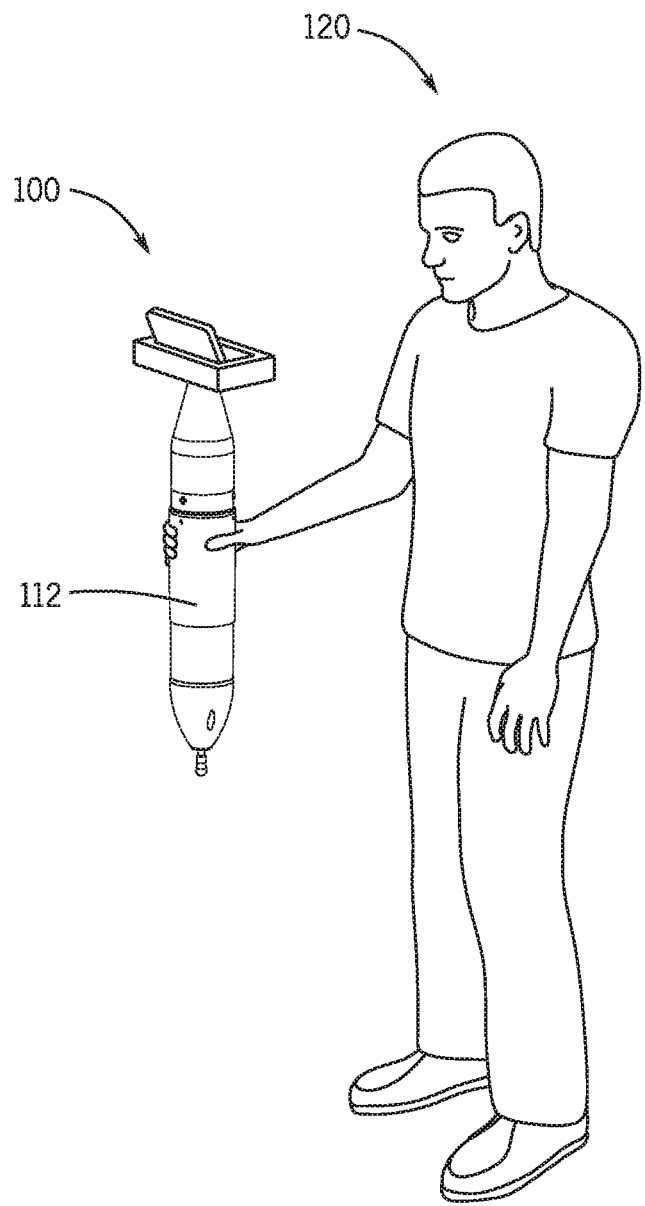
FIG. 2B depicts the elongate probe for handheld use.

Referring to the system configuration of FIG. 2B, the elongate probe 112 may be removable from the UAS 108 and/or ground vehicle 118 for handheld operation by a user 120. The elongate probe 112 may be carried by the user 120 to one or more target locations. During operation, the user 120 positions the elongate probe 112 to more easily access target locations and/or adjusts the length and/or orientation in order to direct the sensor package 106 toward a particular target location. Alternatively, according to some embodiments the elongate probe 112 is a stand-alone device that is not coupled with either the UAS 108 or the ground vehicle 118. Still further, the sensor package 106 and elongate probe 112 may take on a variety of form factors including shapes and/or sizes that are not elongate, but are square, rectangular, cylindrical, spherical, or any other suitable form. Accordingly, probe devices disclosed herein may be transported by one of a variety of ways to target locations for data acquisition. It will be recognized that, in some embodiments, the composition of the elongate probe 112 and/or sensor package 106 neither requires nor is limited to each and every one of the components described herein. The elongate probe 112 may be modified based on whether the probe 112 will be used with the UAS 108, the ground vehicle 118, and/or handheld by the user 120. Furthermore, the components/features of the crop monitoring system 100 may be similarly modified to suit the particular host platform. For example, while the probe device 10 of FIGS. 1A-2A, 3-8, 10A, and 10B is depicted as coupled to the UAS 108, it will be recognized that many components provide the same or similar functionality in the implementations of the probe 112 on the ground vehicle 118 and/or handheld by the user 120.

Operation of the elongate probe 112 may be managed, at least in part, by one or more mobile devices. For example, data acquisition and/or communication with a remote database, electronic storage, and/or processor may be performed by an associated mobile device. Alternatively or in combination, operation of the elongate probe 112 may be independent of an associated mobile device, and even independent of the user 120, instead operating autonomously. For example, data acquisition and/or communication may be integrated into the elongate probe 112 or elsewhere in the system 100, including within a housing assembly 184, as shown in FIG. 6. According to example embodiments, as shown in FIG. 6, the housing assembly 184 may include communications and interfacing connections for a removable memory device (e.g., USB memory stick). Still further, the controller and/or computing device 114 may be disposed within the housing assembly 184.

Additionally or alternatively, in vehicle-based implementations of the system 100, wired or wireless communications and interfacing connections may be provided between the elongate probe 112 and a vehicle (e.g., the aerial vehicle 108 or ground vehicle 118) to which the elongate probe 112 is mounted. Such communications and interfacing connections may be provided in addition to or in place of the connections described above for a mobile device and a removable memory device. By way of further example, the elongate probe 112 may communicate with a mobile device and/or another external device via the UAS 108 when mounted thereon. In this way, remote communications equipment, such as antennas, do not need to be duplicated within the system 100. Portions of processing, storage, and control of the system 100 may be web-based and/or cloud-based, and communication between the elongate probe 112 and UAS 108 with remote data processing and/or storage units is primarily or entirely wireless.

Still further, the elongate probe 112 may include a GPS device for location tracking and/or time tracking. Alternatively or in combination, the elongate probe 112 may utilize a GPS device of the UAS 108, if such a device is already present therein. Accordingly, images captured and data acquired with the elongate probe 112 may be geotagged based on data from the GPS device.

Figure 10B:
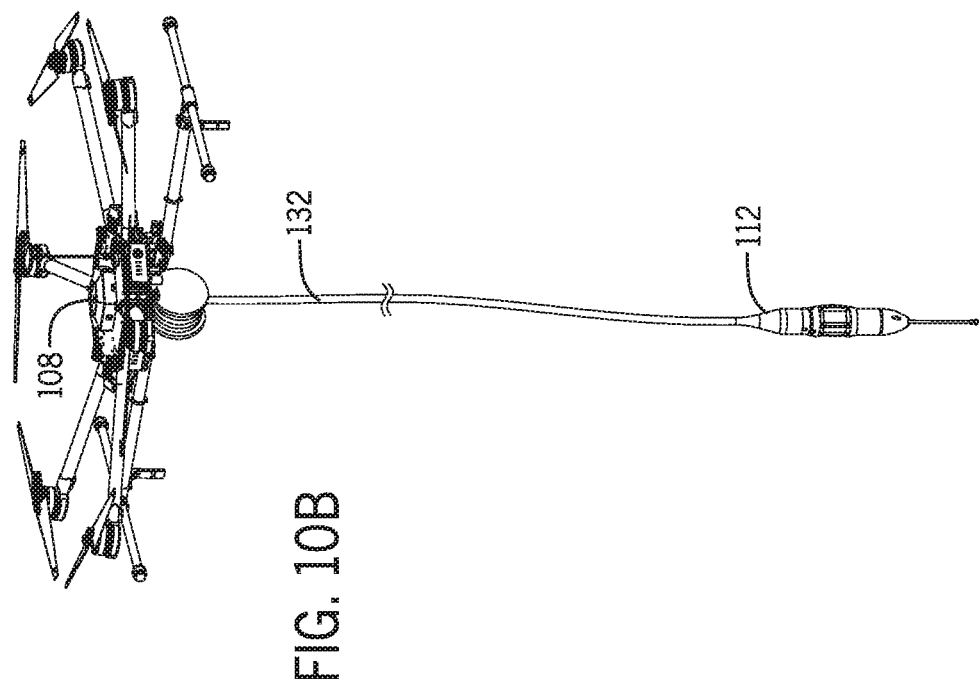
FIGS. 10A and 10B depict isometric view from below of a crop monitoring system including an elongate probe, flexible element, and unmanned aerial vehicle.
Figure 10A:
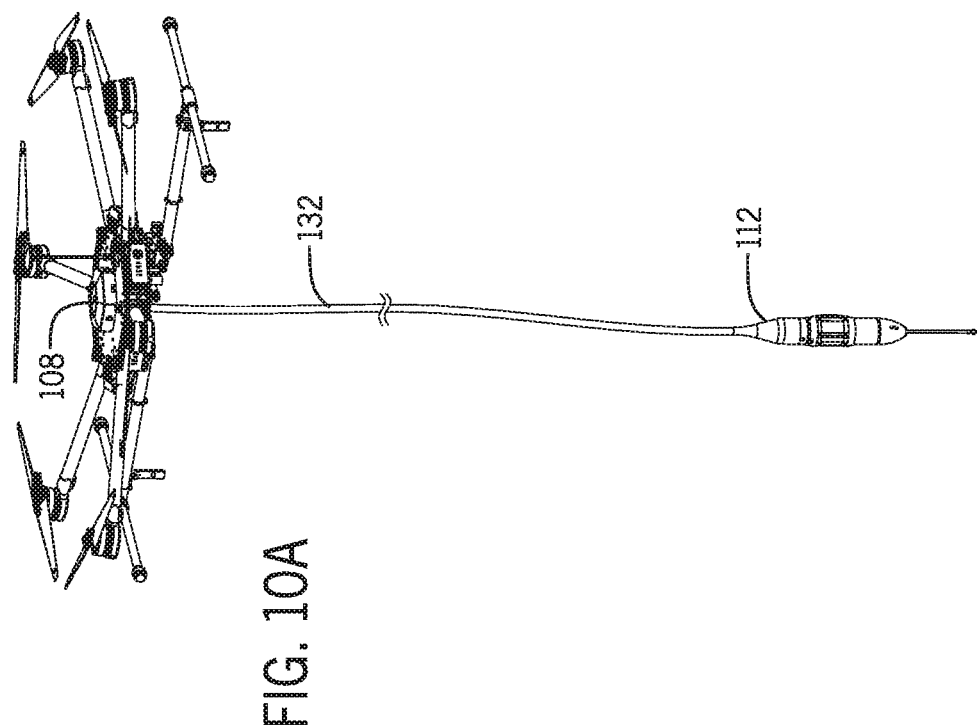

Referring now to FIGS. 1A-1D, 3 and 4, the retractable boom assembly 110 includes rigid arms 124a-f having flexible hinges 126a-f disposed therebetween and operatively coupling one to the next. The combination of rigid arms 124a-f and flexible hinges 126a-f allow the elongate probe 112 to move from a first, retracted position 128 proximal the lower portion 116 of the UAS 108 to a second, extended position 130 distal from the lower portion 116 of the UAS 108, and vice versa. Further, the flexibility of the hinges 126a-f provides a desirable flexibility and/or resilience during flight (see FIGS. 7A and 7B). Referring ahead now to FIGS. 10A and 10B, flexibility and resilience of a connection component 132 between the UAS 108 and the elongate probe 112 may be obtained through a combination of cables, ropes, chains, hoses, and reels or similarly suitable components.

Figure 3:
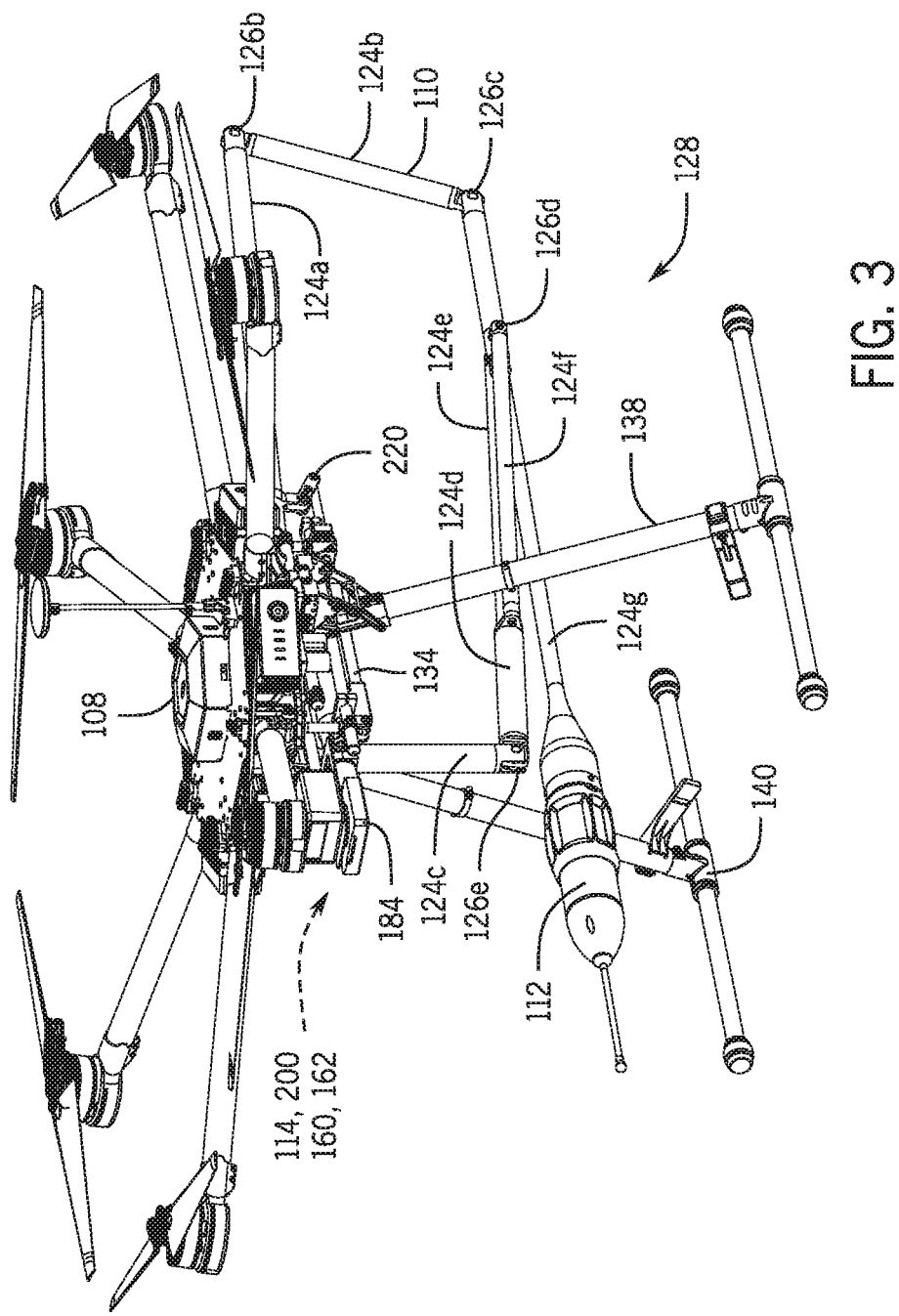
FIGS. 3 and 4 depict a front isometric view from above and a side elevational view, respectively, of the system of FIGS. 1A-D with the retractable boom assembly in a retracted position.
Figure 4:
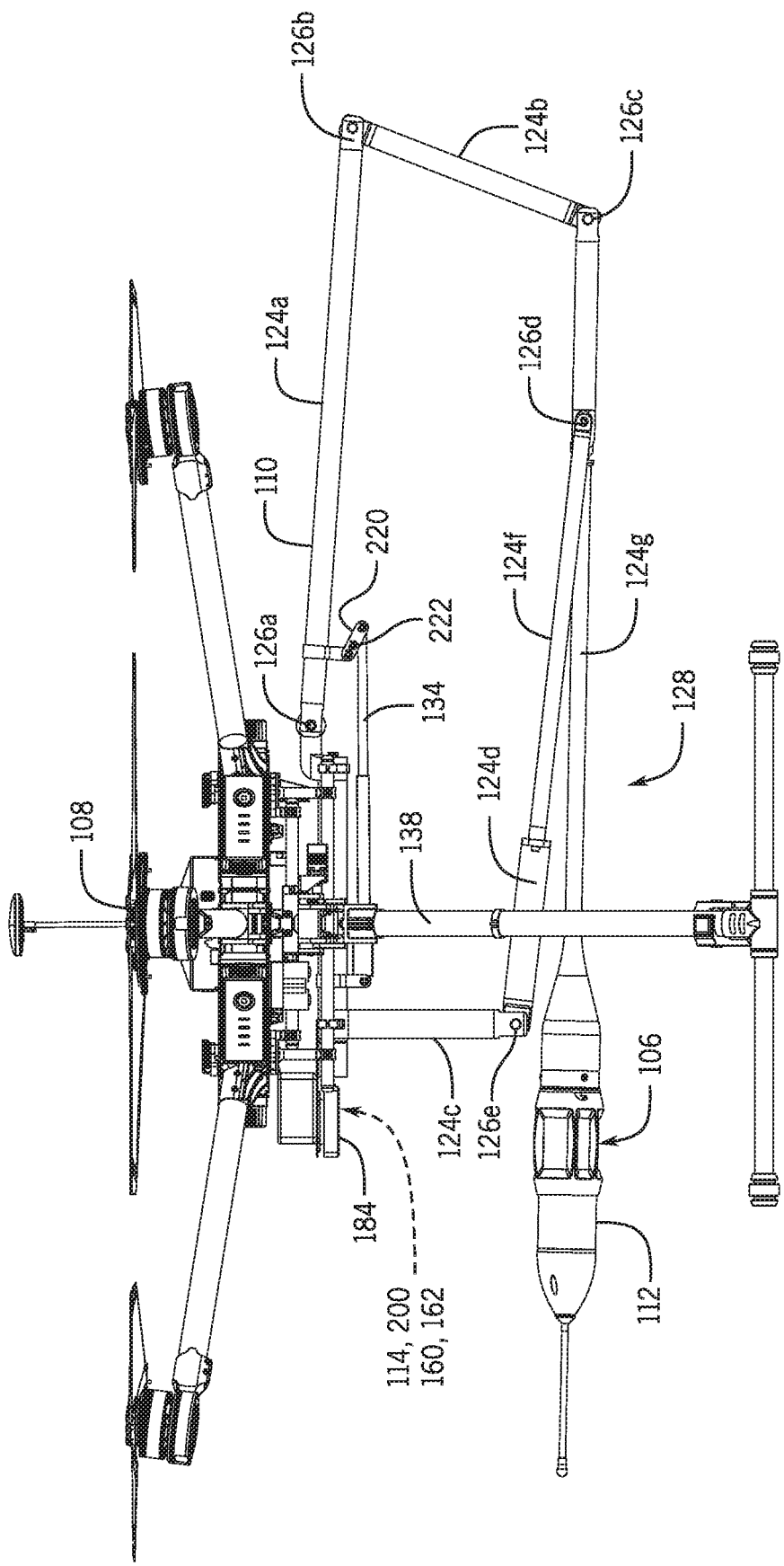
Figure 5:
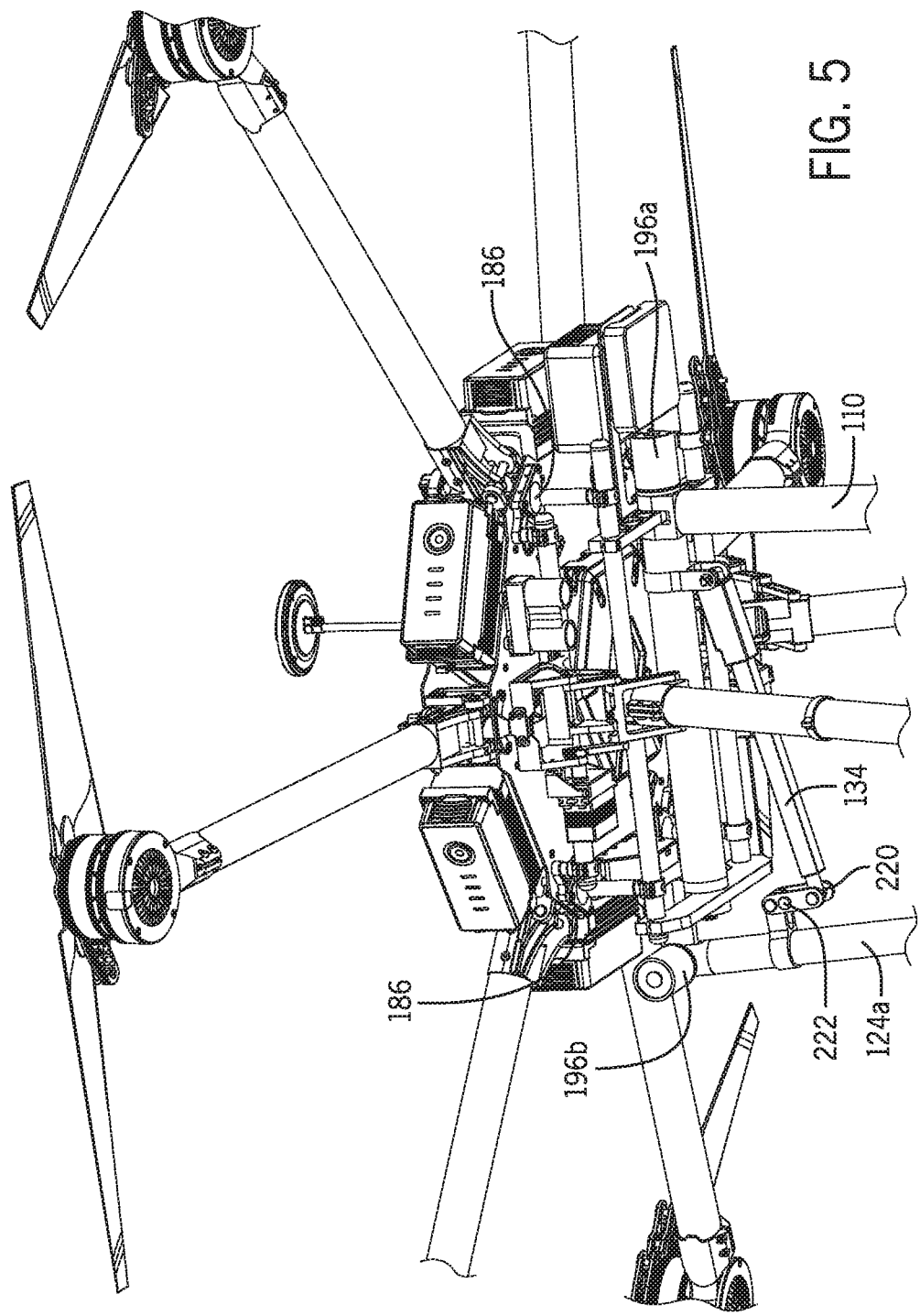
Figure 7A:
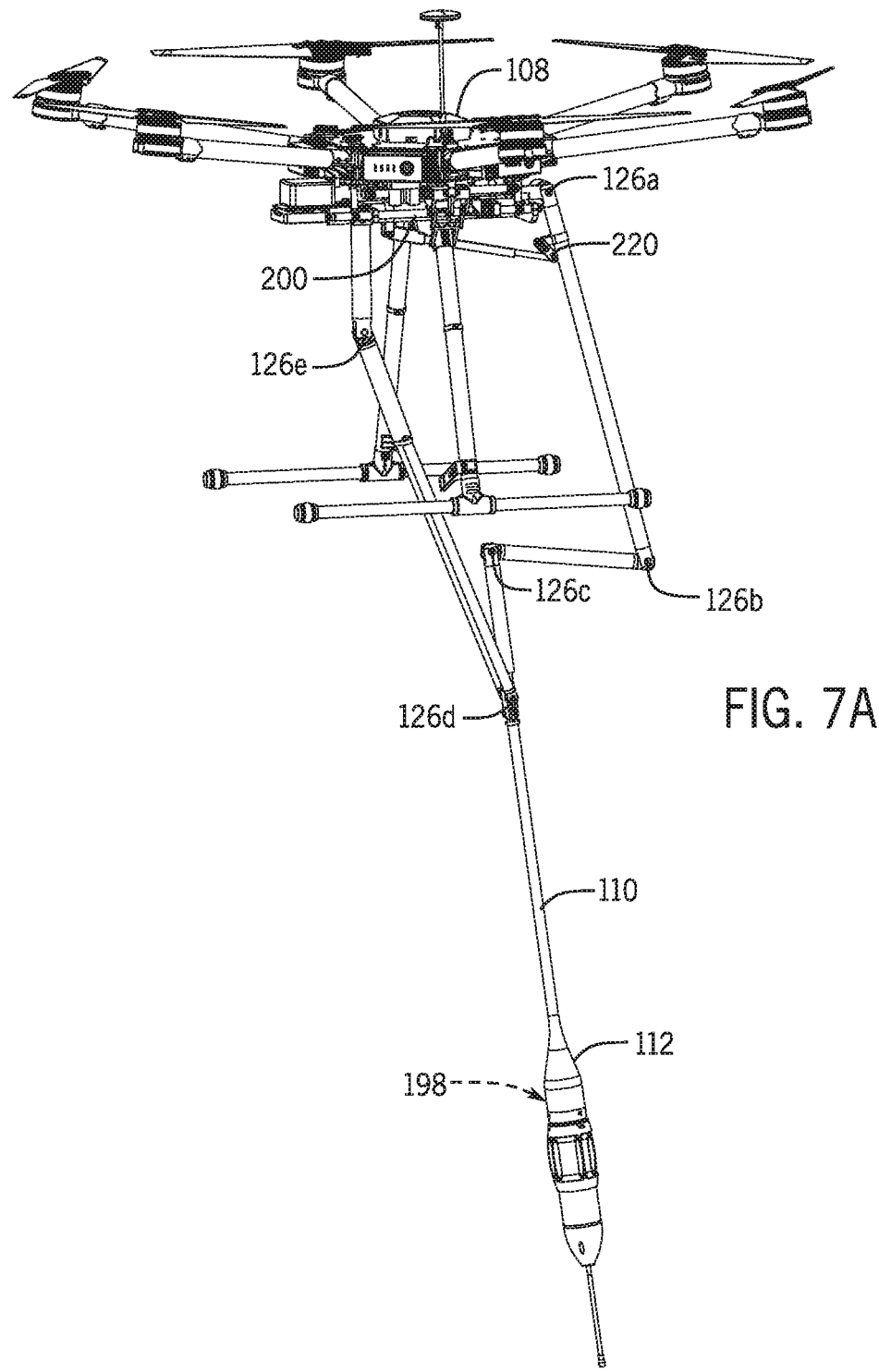
FIGS. 7A and 7B depict isometric views from below and above, respectively, of the system of FIGS. 1A-1D in flight.
Figure 7B:
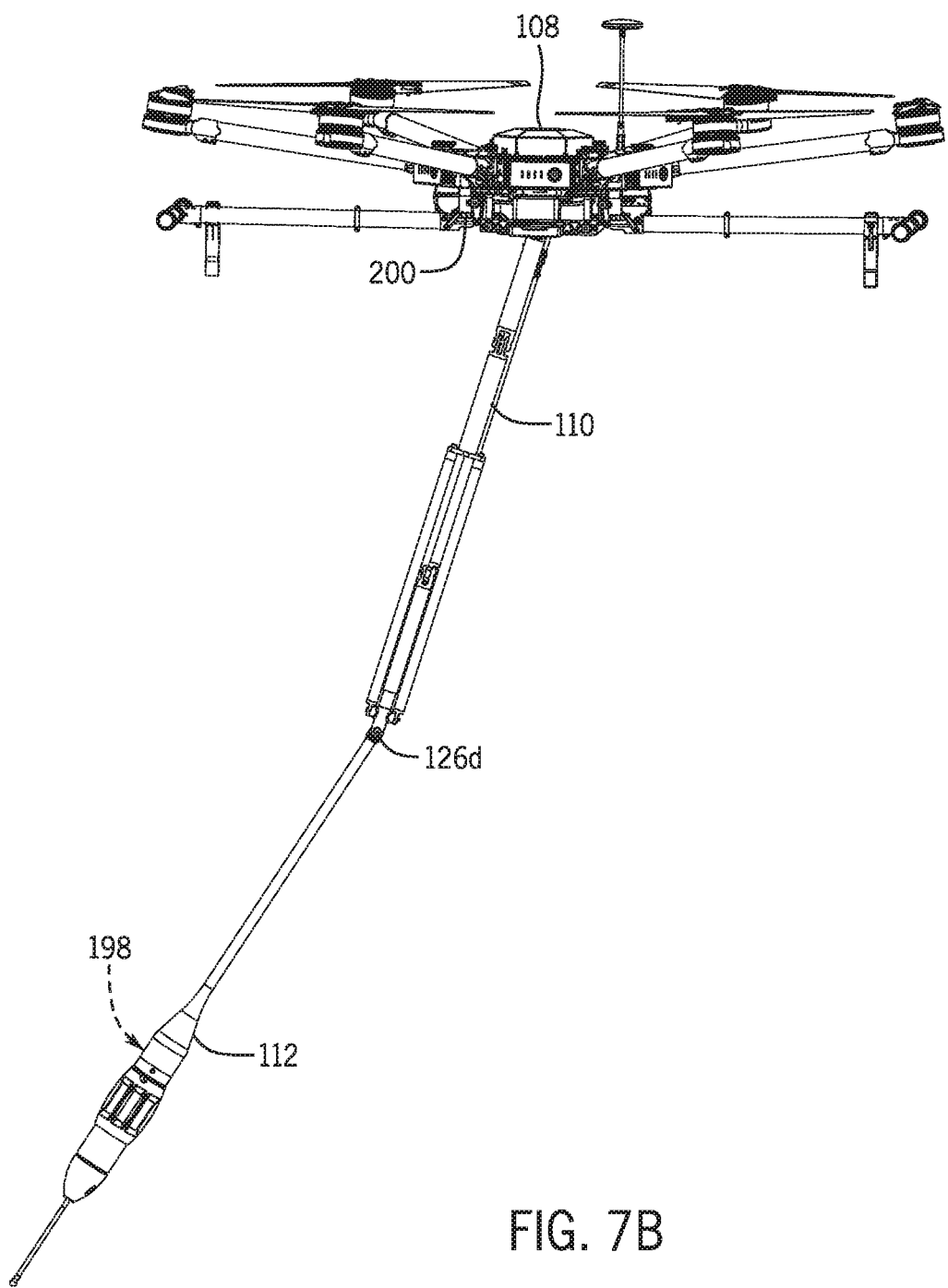

The length of the retractable boom assembly 110 may vary according to the type of crop to be monitored and an associated canopy height thereof. Referring to FIGS. 3, 4, and 5, one or more linear actuators, electric motors, winches, and/or any other suitable actuators 134 may operate to extend and retract the retractable boom assembly 110. The actuator 134 is operatively coupled to the arm 124a by a flexible actuator hinge 220. When the actuator 134 exerts force against the flexible actuator hinge 220, and against the arm 124a through same hinge 220, the actuator hinge 220 initially flexes/hinges about an axis thereof. Once the actuator hinge 220 reaches a certain point, same hinge 220 contacts a restricting pin 222 that prevents further rotation and begins the transfer of energy from the actuator 134 to the arms 124a. As shown, the crop monitoring sensor package 106 is mounted on an end 136 of the retractable boom assembly 110 and other navigational sensors (e.g. microwave radar) may be attached to the upper portion of the retractable boom assembly 110. During launching and landing the retractable boom assembly 110 will remain rigidly in the first, retracted position 128. Retaining the boom assembly 110 in the retracted position 128 during launching and landing protects the sensor package 106 and provides for the first and second landing legs 138, 140 to extend beyond the retractable boom assembly 110. Further, during operation, and while in-flight, the retractable boom assembly 110 extends to the second, deployed position 130. When the retractable boom assembly 110 is in the second, extended position 130 the sensor package 106 extends well beyond the first and second landing legs 138, 140 thereby facilitating the "dipping" of the elongate probe 112 (again see FIG. 28) below the crop canopy 102.

Figure 8:
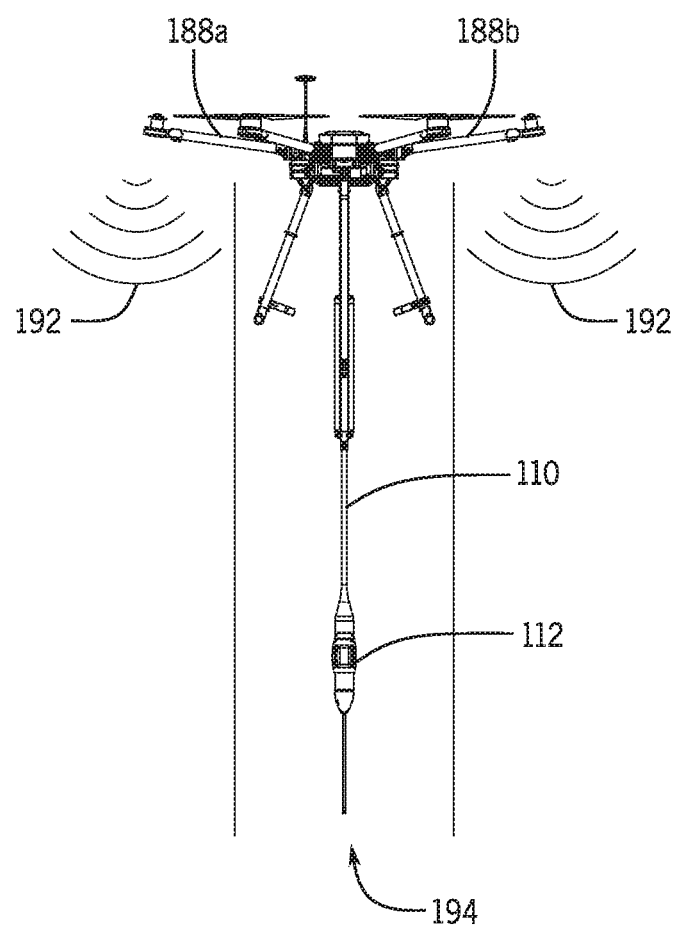
FIG. 8 depicts a schematic of the system of FIGS. 1A-1D with relatively long rotor arms.

The UAS 108 may be transported to a field or launch site with the retractable boom assembly 110 attached and in the first, retracted position 138. In alternative embodiments, the retractable boom assembly 110 may be detached and re-attached to the UAS 108 after and before launch, respectively. The retractable boom assembly 110 may be mounted to the UAS 108 with one or more quick connectors 186. The one or more quick connectors 186 may provide structural attachment as well as power transfer to the sensor package 106 from a power source on board the UAS 108. The quick connector attachment feature may provide for the desirable option of transporting the UAS 108, retractable boom assembly 110, and elongate probe 112, separately and safely from field to field. In example embodiments, the UAS 108 may be a hybrid-powered multicopter so as to leverage the desirable endurance and hovering abilities thereof. Also, as depicted by FIG. 8, in some example embodiments, the multicopter may have relatively long rotor arms 188a-f so as to minimize the downward thrust affecting the insects and crop leaves near the sensor package 106. In this embodiment, the rotor arms 188a-f extend away from a body 190 of the UAS 108. Propeller downwash 192 from rotors supported by the long rotor arms 188a-f is directed to a space away from the retractable boom assembly 110 and elongate probe 112. Thus, a "dead zone" 194 is developed directly underneath the body 190 of the UAS 108. In addition to minimizing effects on insects, leaves, or other observables below the UAS body 190, the extended rotor arms 188a-f may increase stability of the system 100 by decreasing the effect of propeller downwash 192 on the relatively less stable length of the extended retractable boom assembly 110.

Referring again to FIGS. 1A-1D and 3-5, when the retractable boom assembly 110 is in the first, retracted position 128, the boom assembly 110 is locked in place and relatively rigid so that swinging, or other movement, of the boom assembly 110 and elongate probe 112 does not add outside inertial forces during launching and landing operations. By folding and retracting the boom assembly into the relatively rigid and compact first, position 128, the center of gravity of the boom assembly 110 and sensor package 112 is aligned more closely with the center of gravity of the UAS 108, therefore minimizing the moment of inertia for the system 100. The first, retracted position 128 of the retractable boom assembly 110 provides for normal UAS launching and landing procedures and ensures safe operation thereof. Still further, the first, retracted position 128 assists in protecting the elongate probe 112 and sensor package 106 by tucking the sensor package 106 between the legs 138, 140 of the UAS 108 and near the lower portion 116 of the UAS body.

Figure 9C:
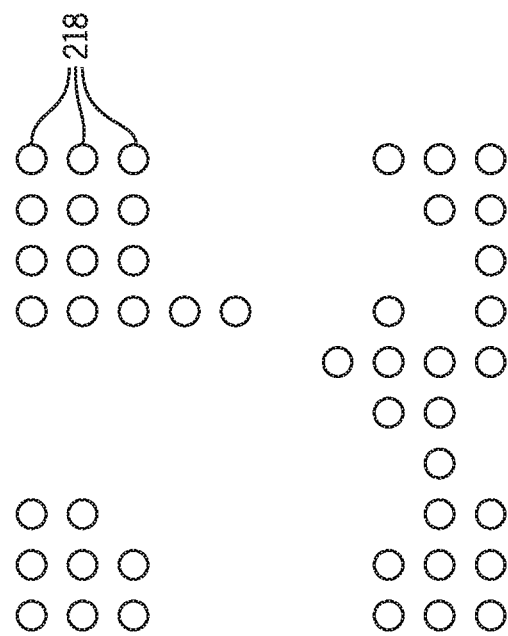
FIGS. 9B and 9C depict graphical representations of flight patterns for the system.
Figure 9B:
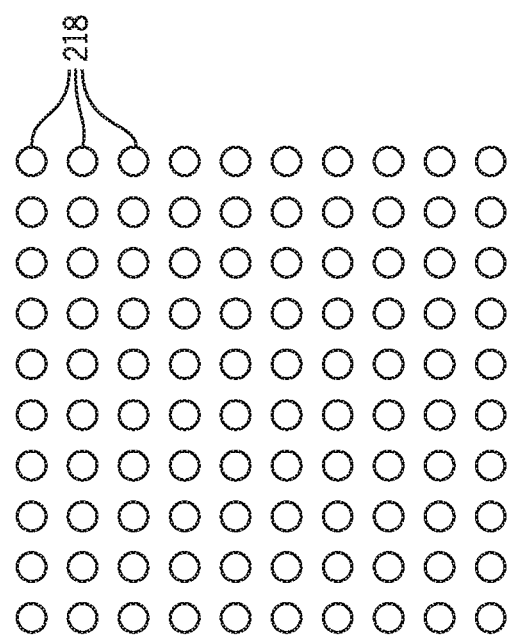

As illustrated by FIGS. 9B and 9C, when the system 100 operates a monitoring mission, the UAS 108 may navigate in a grid sampling pattern (FIG. 9B) or smart sampling pattern (FIG. 9C) based on data such as an NDVI (Normalized Difference Vegetative Index) map. After the UAS 108 reaches a safe altitude based on observations of an internal GPS as compared with a safe altitude determined by UAS 108 pre-programmable software, the retractable boom assembly 110 is deployed to the second, extended position 130. When the retractable boom assembly 110 reaches the operational, extended position 130, the elongate probe 112 is flexible at the hinges 126a-f so that inertial moments are not transferred from the sensor package 106 and retractable boom assembly 110 to the UAS 108. A failure to account for the inertial moments of the retractable boom assembly 110 may result in decreased flight performance, decreased stability, and potential unplanned landing of the UAS 108. FIGS. 7 and 8 depict the system 100 in flight with the retractable boom assembly 110 flexing according to acceleration and inertial forces acting thereon.

The retractable boom assembly 110 may include roll axis and pitch axis energy dampening mounts 196a, 196b, as shown in FIG. 5. The energy dampening mounts may be rubber dampers, rubber bands, and/or hydraulic or air shock absorbers. These dampening devices 196a, 196b improve quality for images and sensors observations captured by the sensor package 106 by decreasing vibrational noise experienced thereby. Still further, the dampening mounts 196a, 196b may improve the flight stability of the system 100 by decreasing movement of the retractable boom assembly 110. Decreasing vibration may desirably increase longevity of both mechanical and electronic equipment attached to the UAS 108 and retractable boom assembly 110.

However, the flexibility of the retractable boom assembly 110, illustrated in FIGS. 7 and 8, does not completely eliminate energy transfer from the retractable boom assembly 110 and elongate probe 112 to the UAS 108. Therefore, a first IMU (Inertial Measurement Unit) 198 is disposed within the sensor package 106 to measure the speed and acceleration of the elongate probe 112. Inertial measurement unit ("IMU") devices measure magnetic heading, probe orientation, and linear or angular accelerations with respect to the earth. For example, IMU devices may include a 3-axis accelerometer, a 3-axis gyroscope, and/or a 3-axis magnetometer. Further, IMUs measure and/or provide data for determining position, orientation, speed, and/or acceleration of the elongate probe 110.

Figure 28:
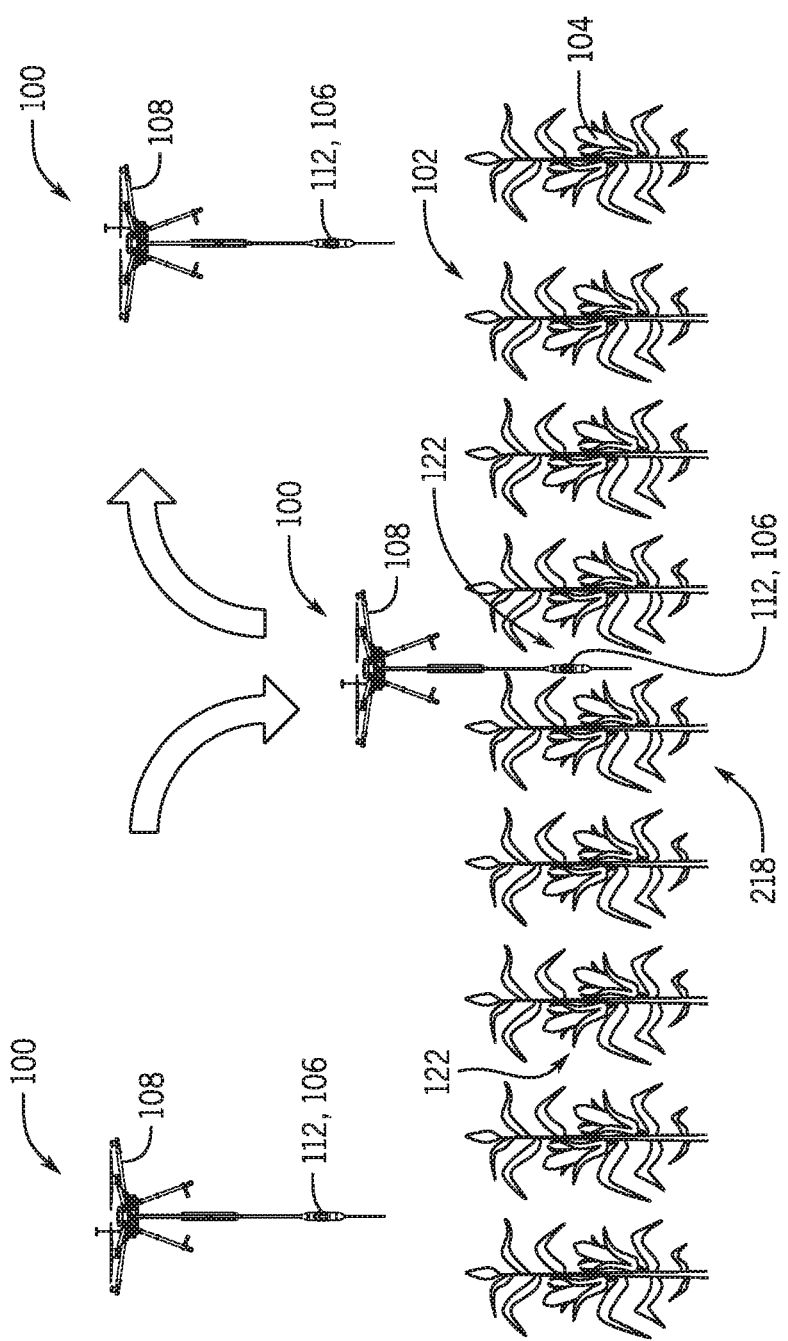
FIG. 28 is a schematic of a crop monitoring system performing a dipping maneuver.

The data from the first IMU 198 may be used in conjunction with a second IMU 200 disposed in or on the UAS 108. With the data from the combination of IMUs, the extent of the retractable boom assembly 110 with the weight of the elongate probe 112 may be used similar to a pendulum inertia damper negating the forces applied to the UAS 108 from the boom assembly itself. This process shares some properties with noise canceling. The data gathered by the first and second IMUs 198, 200 may be used to control the speed, direction, and acceleration of the UAS 108 such that forces acting on the UAS 108 are absorbed and stable flight is maintained. Further, the IMU inputs, may be processed such that the weight of the elongate probe 112 is used as a counter balance to rapidly slow down the drone, resulting in improved flight efficiencies. Referring to FIGS. 10A and 10B, for example, if the retractable boom assembly 110 swings in a first direction, the first IMU 198 will communicate same to the controller/processor 114 (FIG. 9A). In response to the observations of the first IMU 198, the controller 114 instructs the UAS 108 to navigate in a direction opposite the swinging of the retractable boom assembly 110 thereby calming and settling the forces acting on the system 100. Furthermore, the controller 114 may use inputs from both the first and second IMUs 198, 200 to determine a stable flight pattern or to react to shifting forces in-flight. The first and second IMUs 198, 200 are in consistent communication with the controller 114 and the navigational controls of the UAS 108 in order to maintain safe, stable flight during flight to and from locations within the grower's field as well as during the dipping maneuver described hereinthroughout (FIG. 28).

Referring now to FIGS. 11A-E, the elongate probe 112 at the end of the retractable boom assembly 110 is designed for insertion into the canopy 102 of the crop 104 to be monitored. The elongate probe 112 is compact and cylindrical in shape. Further, an outer surface 142 of the elongate probe 112 is smooth. The outer surface 142 of the elongate probe 112 may comprise acrylic, glass, polyurethane, aluminum, carbon-fiber composite, borosilicate glass, and/or another suitably smooth and preferably light material. Further, cylindrical middle portion 154 of the elongate probe 112 is a least partially housed by an optically transparent surface 168 comprising a protective composite shell or glass outer surface that provides visibility for the operation of optical sensors, detailed hereinbelow, of the sensor package 106.

Conical end caps 144, 146 are disposed at upper and lower ends 148, 150 of the elongate probe 112. The smooth outer surface 142 and conical end caps 144, 146 aid in preventing entanglement of the elongate probe 112 in any dense vegetation of the crop 104. Preventing entanglement of the elongate probe 112 may provide benefits including improved sensor performance and prevention of altitude loss resulting from entanglement of the elongate probe 112 creating downward forces on the UAS 108.

Referring now to FIGS. 12A-14, partly in order to achieve the compact design mentioned above, the layout of optical sensors, LEDs, and cameras in the sensor package 106 optimizes data capture by the elongate probe 112 while dipped within the space 122 below the crop canopy 102. One or more cameras 152a-c are disposed about the elongate probe 112 on interior sensor mount surfaces 170a-c and are directed horizontally outward therefrom. The cameras 152a-c are arranged radially and symmetrically within the cylindrical middle portion 154 of the elongate probe 112, inside the optically transparent surface 168. The cameras capture images up to 360 degrees radially about an axis 166 of the elongate probe 112. In some example embodiments, multiple image views may be combined to provide radially outward imaging entirely about the axis 166. Additionally, one or more luminous flux sensors 156a-c and one or more LiDAR sensors 158a-c are similarly arranged radially and symmetrically within the cylindrical middle portion 154. The luminous flux sensors 156a-c and LiDAR sensors 158a-c are disposed in substantially axial alignment with the respective cameras 152a-c on the sensor mount surfaces 170a-c and are likewise directed horizontally outward therefrom. In the embodiment(s) shown in FIGS. 12A and 12B, the luminous flux sensor(s) 156a, 156b, cameras 152a, 152b, and LiDAR sensors 158a, 158b, are vertically aligned from top to bottom on each sensor mount surface 170a-c. Additionally, the cameras 156a-c, and other sensors, are offset 120-degrees from one another. Alternatively or in combination, one or more of the above-described sensors may be directed, at least in part, along the longitudinal axis 166 of the elongate probe 112 (e.g., toward the upper and/or lower ends 148, 150 of the elongate probe 112).

Once again referring to FIGS. 3-5, according to some embodiments, a downward facing camera/sensor 160 may be disposed on the lower portion 116 of the UAS 108 for observation of crops with broad upward facing leaves. Further, the downward facing camera 160 may capture images of crops from an altitude substantially above the canopy 102 rather than during the dipping maneuver. The downward facing camera 160 may capture images while the UAS 108 navigates over monitored crops to give the grower (s) context concerning the sampling area. Additionally, the downward facing camera 160 may, perhaps in conjunction with a downward directed radar 162 also disposed on the lower portion 116 of the UAS 108, be used to determine current altitude for the UAS 108 and/or calculate a distance to the canopy 102 for the purpose of pre-determining a flight path during a forthcoming dipping maneuver. Distance to the canopy 102 may also be calculated in real time by the downward facing camera 160, radar 162, and/or LiDAR during the dipping maneuver.

The cameras 152a-c, 160 may be RGB, thermal, ultraviolet, and/or infrared cameras or another suitable type of camera. According to an example embodiment, active depth sensing camera technology provides some benefits by facilitating analysis of plant leaves at different distances and orientations. Specifically, the depth sensing technology may be used to correct images captured of targets disposed at an angle or other otherwise having a varying depth from the camera. Referring now to FIGS. 12A-13, 16, and 17, one or more multicolor and/or true white (RGB+White) light emitting elements, such as multicolor LEDs 164, are disposed in a vertical configuration in the elongate probe 112, flanking the other sensors described hereinabove. Natural lighting under the crop canopy 102 is subject to significant variation. Therefore, the multicolor LEDs 164 supply lighting for each camera 152a-c during operation below the crop canopy 102. The LEDs 164 can include a capability to emit ultraviolet ("UV") light, and the cameras 152a-c may be capable of capturing reflected UV light for diagnostic or other purposes. The cameras 152a-c may balance characteristics of a captured image, such as, for example, captured images of a crop or plant may be balanced for color correction (e.g., white balance), brightness, and contrast. For example, a light source (e.g., light emitting element 164 of the elongate probe 112 and/or natural daylight) may be identified as a basis for image corrections. Subsequently, such corrections may be made automatically or manually, in real time or during post image capture processing.

The LEDs 164 may be used in combination with data acquired from the luminous flux sensor(s) 156a-c to ensure optimal lighting for image capture in both daytime and nighttime conditions. Further, the LEDs may provide additional illumination when the crop canopy 102 is sufficiently dense to obstruct sunlight from reaching the space 122 beneath the crop canopy 102. Additionally, particular insects and diseases react differently to illumination characterized by different colors, color temperature, and/or brightness. Therefore, the multicolor LEDs 164 in the sensor package 106 may be configured to provide light with a variety of colors, color temperatures, and/or intensities, accordingly.

As noted above with reference to FIGS. 12A-15, the three horizontally mounted LiDAR sensors 158a-c are each focused in line with respective cameras 152a-c. Such sensor alignment provides for micro-positioning and nudging of the UAS 108 navigation mid-flight in some embodiments discussed hereafter. For example, if the one or more LiDAR sensors 158a-c detect a leaf or other obstruction within a predetermined proximity to the camera lens, the processor 114 associated with the sensor package 106 may instruct UAS 108 to move evasively, such as in the opposite direction from the obstruction or rotationally about an axis of the UAS 108. Such evasive maneuvers may improve the quality of an image captured by the one or more cameras 152a-c by moving or avoiding the obstruction. This operation, using the LiDAR sensors 158a-c to make small navigational corrections to the UAS 108, may be referred to as "nudging" and/or "micro-positioning" functions of the system 100.

While the above example considers use of cameras in conjunction with LiDAR sensors, micro-positioning and/or nudging functions may utilize a variety of sensors and/or sensor combinations. Depending on crop conditions, the one or more microprocessors/controllers 114 associated with the sensor package 106 may determine a combination of sensor data to be used for calculating optimal micro-positioning and nudging adjustments. Alternatively, sensor combinations used for micro-positioning and nudging may be selectively determined by a grower or system operator.

Nudging is controlling small navigational movements of the UAS 108 in all three axes to acquire an optimal image capture by one or more of the cameras 152a-c. As a further example, when navigating dense crops, the microwave radar 162 may measure an average height, or distance from the UAS 108, of the crop canopy 102. However, in relatively less dense crops such as orchards, a combination of the microwave radar 162 and one or more LiDAR sensors 158a-c may be used to differentiate between spaces between individual plants and the actual canopy 102 of the crop 104.

By way of further example, one or more luminous flux sensors 156a-c may be used to determine when the sensor package 106 has entered the space 122 inside the crop canopy 102. As the UAS 108 decreases altitude towards the crop canopy 102, the luminous flux sensors 156a-c actively read the brightness of the area surrounding the sensor package 106. When the intensity of the measured light suddenly decreases, such a change indicates that the sensor package has entered the space 122 beneath the crop canopy 102. This data may then be used to verify a true position of the UAS 108 and sensor package 106. In further example embodiments, micro-positioning may be used to move a target, such as a leaf or insect, towards the center of the image frame of the one or more cameras 152a-c. In such an example embodiment, the cameras 152a-c may be set to capture video. Then following detection of an insect or disease lesion in the image frame, the UAS 108 may be instructed to "nudge" in a selected direction to center the target within the image frame. Once the target is centered in the image frame, the associated camera(s) 152a-c may automatically capture a still image before the UAS 108 proceeds to a next target.

Figure 16:
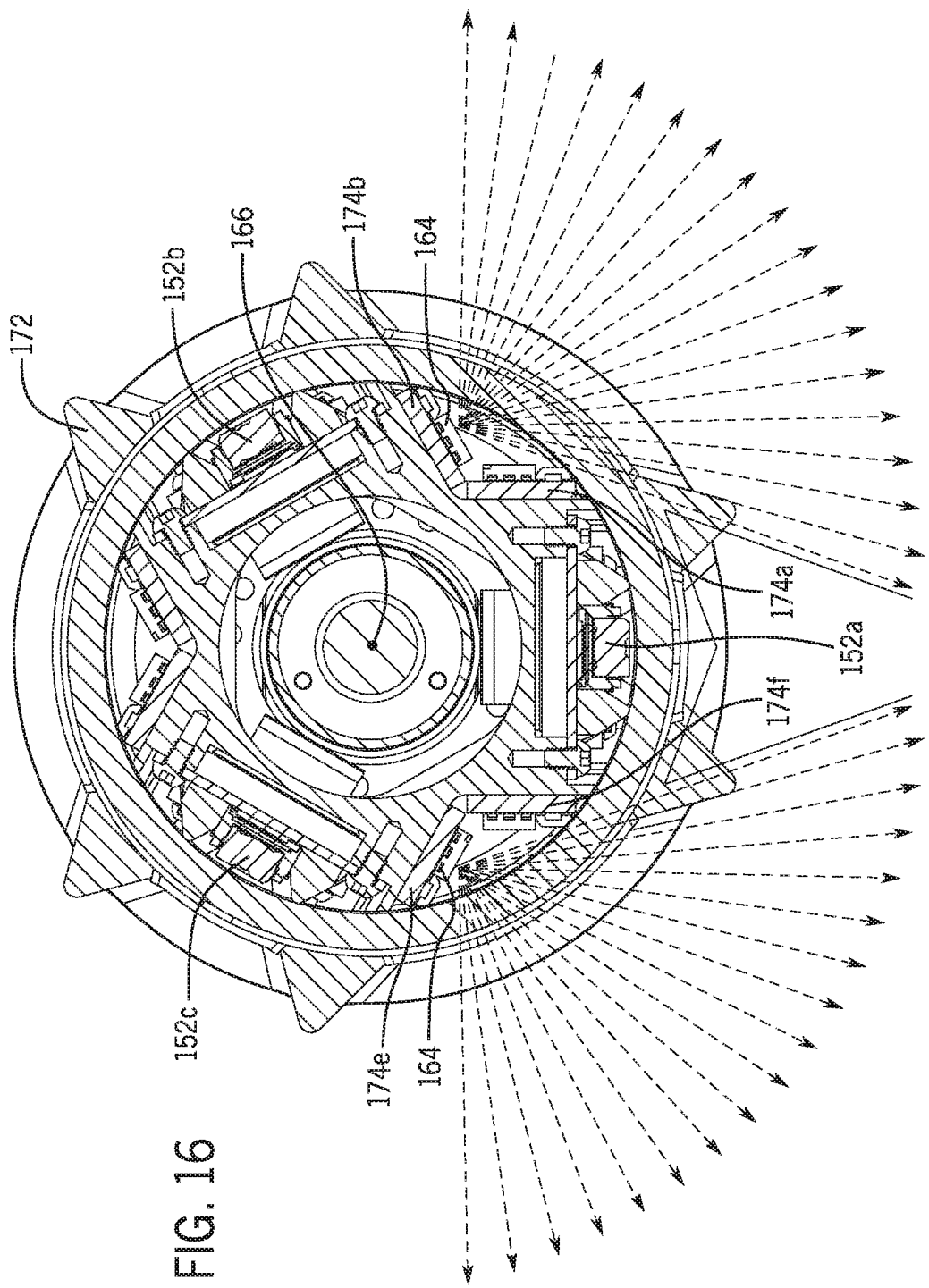
FIGS. 16 and 17 are cross-sectional views of the elongate probe taken along line B-B of FIG. 11A, further depicting LED ray trace diagrams.
Figure 17:
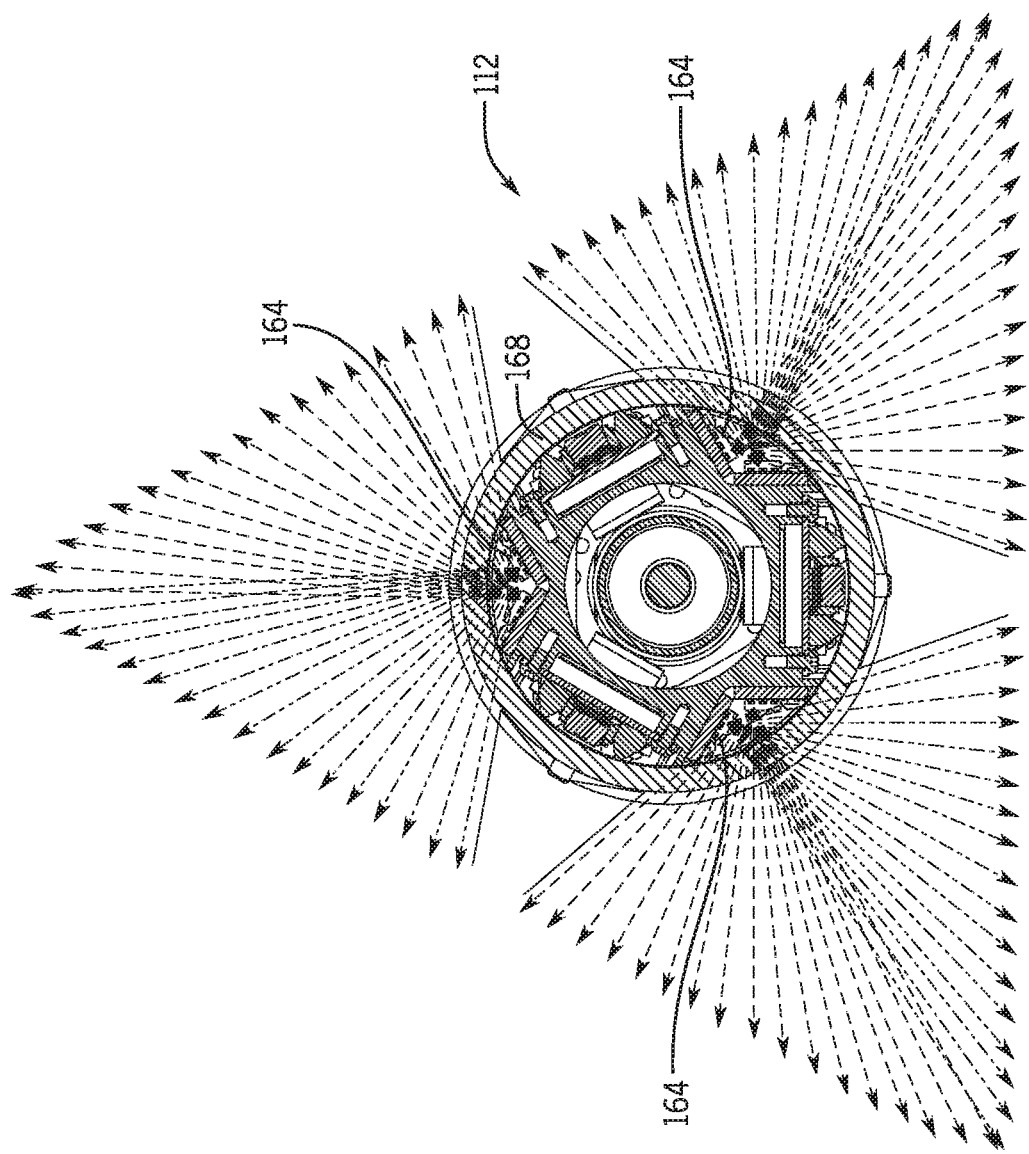

Referring now to FIGS. 16 and 17, ray trace diagrams of light provided for each of the cameras 152a-c are depicted. In these example embodiments, a housing of the sensor package 106 is designed to improve the quality and reliability of data capture. Columns of LEDs 164 are disposed on mounting surfaces 174a-f of mounting bracket 176, while the cameras 152a-c, LiDAR sensors 158a-c, and luminous flux sensors 156a-c are separately mounted on sensor mount surfaces 170a-c. With this configuration, the physical mounting bracket 176 separates the sensors and the LEDs 164 such that the light from each LED column illuminates a space corresponding to the one or more cameras 152a-c associated therewith. This example embodiment allows for three unique LED light colors and intensities, each unique combination thereof corresponding to one of the cameras 152a-c, without interference from one other. The columns of LEDs 164 are arranged in pairs and the pairs thereof are offset from one another by 120-degrees. The triangular configurations formed by the cameras 152a-c and the LED pairs taken as a whole are, in turn, offset from one another by 60 degrees. Additionally, a ridge-shaped heat sink 224 is disposed vertically above and axially aligned with the sensor package 106. The heat sink 224 has ridges disposed thereon that may double as mounting points for optional features.

Figure 15:
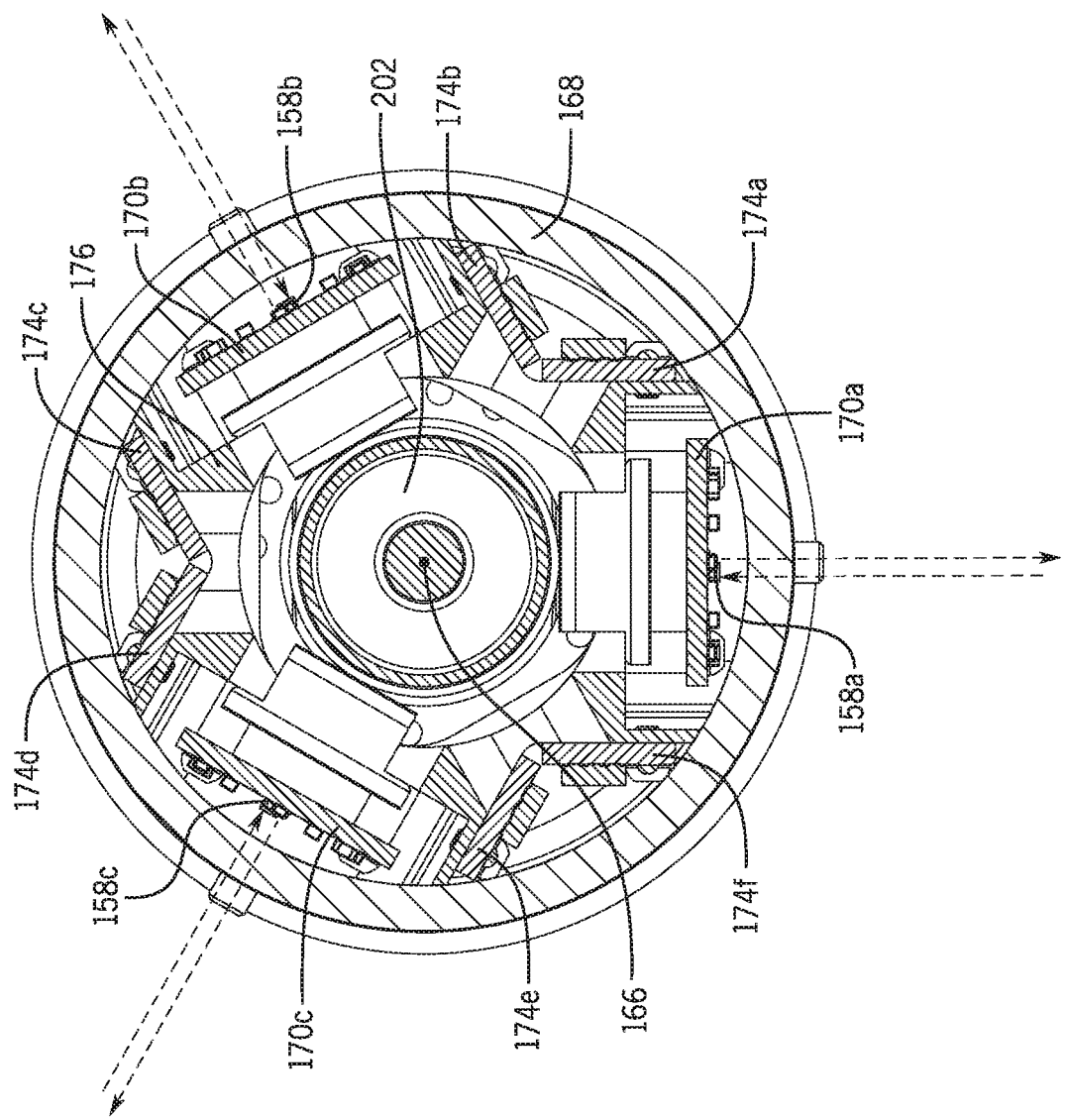
FIG. 15 is a cross-sectional view of the elongate probe taken along line B-B of FIG. 11A, further depicting a diagram of LiDAR sight lines.

As previously described with reference to FIGS. 12A and 12B and shown again in FIGS. 15-17, a housing of the sensor package includes an optically transparent surface 168, such as glass, that covers the sensors and components thereof to protect same from the harsh environment under a crop canopy. Referring back to FIGS. 13 and 14, camera mounts 178a-c are configured such that lenses of the cameras are mounted very close to the inside of the optically transparent surface 168 to decrease glare and distortion resulting from the physical properties of the curved glass, or other transparent material, comprising the optically transparent surface 168. Internal lens hoods formed between the optically transparent surface 168 and each camera lens prevents light emitted by the LEDs 164 from directly entering the lenses while decreasing glare.

Figure 18:
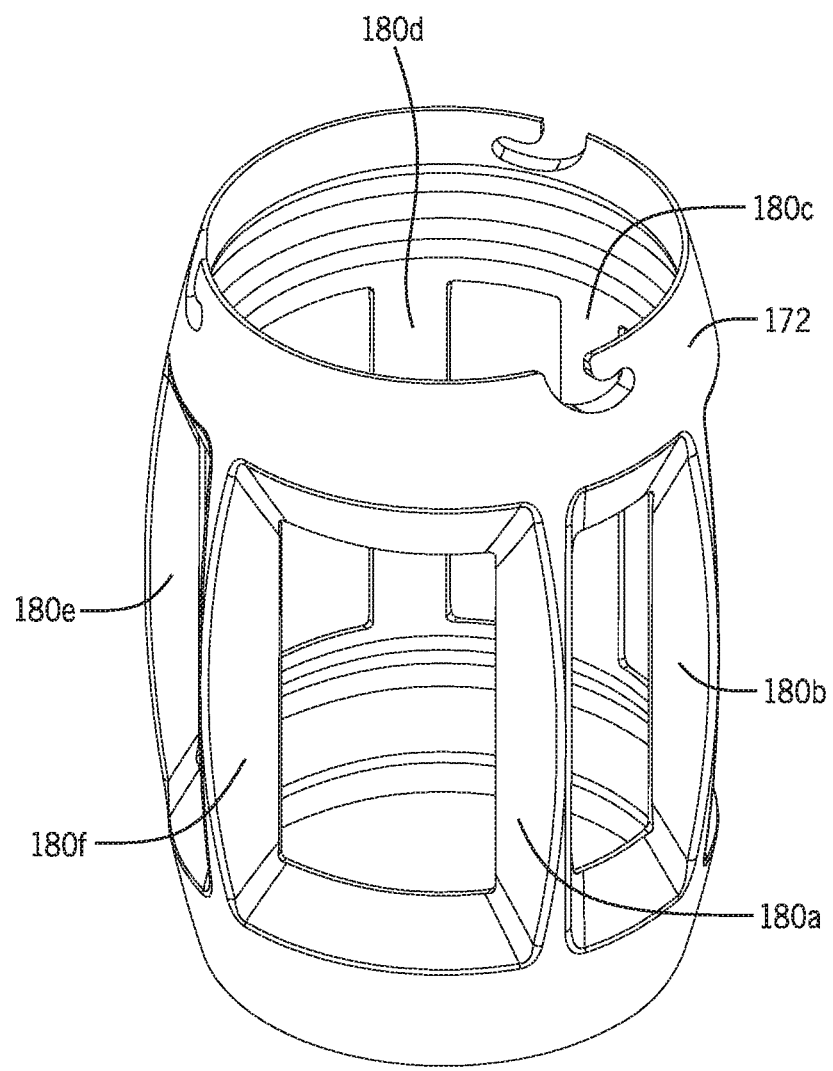
FIG. 18 is an isometric view from above of a sensor package shield with the elongate probe omitted.
Figure 20:
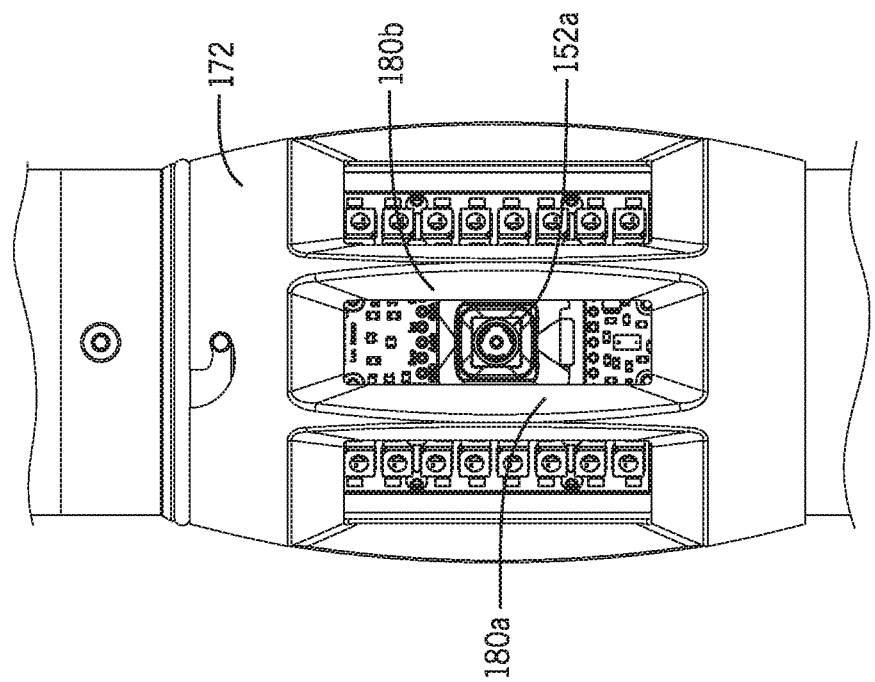
FIG. 20 is a partial, enlarged side elevational view of the elongate probe and sensor package shield of FIG. 19 rotated 60 degrees.
Figure 19:
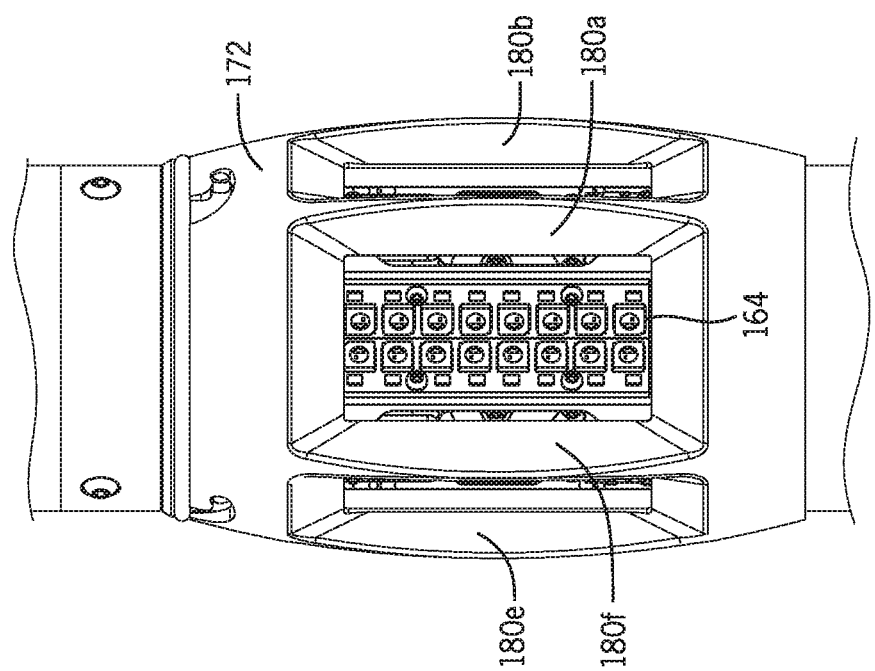
FIG. 19 is a partial, enlarged side elevational view of the elongate probe and sensor package shield.

Referring now to FIGS. 18-20, a sensor package shield 172 is illustrated. In the depicted example embodiment, the sensor package shield 172 is disposed about the optically transparent surface 168. The sensor package shield 172 comprises three pairs of fins 180a-f, each pair located proximal one of the cameras 152a-c. The fins 180a-f physically block debris, such as leaves, insects, and/or soil, from contacting and/or obstructing the optically transparent surface 168 surrounding the sensor package 106. In example embodiments, shrouds, air blasts, and/or physical glass wipers may be used alternative to or in combination with the sensor package shield 172. A bayonet mount comprising bayonet pins 182a-c is disposed vertically above the sensor package 106 to couple the sensor package shield 172 to the elongate probe 112. The same bayonet pins 182a-c may be used to couple alternative embodiments of the sensor package shield 172 that move materials and obstructions away from the sensor package 106. For example, the specific type sensor package shield 172 shape and/or size may be optimized depending on crop type, crop density, crop height and/or other environmental conditions. By way of further example, the sensor package shield 172 shape and/or size may be optimized to decrease likelihood of contact with dew, dust, insect fluids and/or leaves by the optically transparent surface 168 enclosing the sensor package 106. In addition to preventing obstruction of the sensor package 106, the sensor package shield 172 may provide protection of the physical integrity of the sensor package 106 and/or optically transparent surface 168, especially in the event of an unexpected landing.

Other sensors contained in the sensor package 106 may include crop canopy temperature sensors, crop canopy barometric pressure sensors, and crop canopy humidity sensors. Microenvironment data observed thereby may be used to correlate environmental conditions to crop stresses. The sensor package 106 may have a modular design so that different sets of sensors may be swapped one or another. Other modules deployable within the elongate probe 112 include, but are not limited to, fungal detectors, tissue samplers, soil samplers, vacuum tools, and/or other suitable sensors and devices. Modular design of the elongate probe allows same to be swappable with other modalities/platforms such as an ergonomic handle with trigger to create a hand probe, a relatively long handle with a trigger allowing a human user to penetrate the canopy of a tree from the ground, and a mount for ground vehicles such as all-terrain vehicles, tractors, sprayers, and automobiles.

The probe device 10 discussed herein can be controlled based on operation and arrangement of processing units and other electronic components disposed within the elongate probe 112 and/or the housing assembly 184. The controller 114 may be a master processing unit connected to and controlling various components of the system 100, including humidity, and/or barometric pressure sensors, an internal temperature sensor, above- and below-canopy external temperature sensors, a voltage sensor, a current sensor, and a real-time clock. The master processing unit/controller 114 may comprise a plurality of processing/controlling units operating in concert. One or more microcontrollers may be connected to and control various components of the system 100, including the first and second IMUs 198, 200, one or more LiDAR sensors 158a-c, one or more cameras 152a-c, a temperature sensor, and/or other sensors described herein so as to offload processing functions from the main microprocessor(s)/controller 114. Electronic elements may be provided and interconnected to provide the functions described herein. While certain electronic elements are shown as being located in/at the housing assembly 184 and/or sensor package 106, it will be recognized that such elements may be located within other portions of the elongate probe device 112. Also, the system may include one or more power sources (e.g., battery), power conversion components, power sensing components, and fuses. Corresponding structures may be provided within the housing assembly 184, the UAS 108, and/or the elongate probe 112 to support and operably connect the various components.

Once the UAS 108 has navigated to the pre-programmed GPS coordinates, using either a grid or smart sampling method as described with reference to FIGS. 9B and 9C, the system 100 determines a distance to the crop canopy 102 with one or more sensors including, but not limited to, microwave radar, LiDAR, cameras, and ultrasonic sensors such as the downward/facing camera 160 and/or downward directed radar 162 detailed hereinabove. Insects, diseases, nutritional deficiencies, and environmental damage are present at different locations on individual plants depending on the particular stress type and the crop type (e.g., soybean aphids are generally located on the top leaves of a soybean plant, while nitrogen deficiency symptoms are located on the bottom of a corn plant). To account for this variation, the crop type and targeted crop stress may be programmed into memory/storage of the system 100 before launch. The combination of observations by the downward directed microwave radar 162 and pre-programmed crop type and crop target stress information informs the controller 114 when preparing to lower/dip the elongate probe 112 below the crop canopy 102. In accordance with the data input, the UAS 108 dips the elongate probe 112 into the crop 104 to a predetermined depth to increase the likelihood of finding the targeted crop stress. For example, the sensor package may be lowered 18 inches below the top of a corn plant crop canopy to observe a disease such as Goss's Wilt. In example embodiments, sampling may be performed according to specific zones. The zones can be user-defined or automatically detected based on present or past detection of threats. Alternatively, the data provided to a user/grower may be classified according to the sampling zones. The data can include, inter alia, a financial valuation of crop threats found therein.

The insertion depth to which the elongate probe 112 is inserted into the crop may be calculated by subtracting the altitude of the UAS 108 above the crop as determined by the output from the downward microwave radar 162 and/or LiDAR sensors from the combined length of the retractable boom assembly 110 and elongate probe 112. The UAS autopilot receives the IMU 198, 200 and altitude data from the sensor package microprocessor/controller 114 to continually adjust the altitude of the system 100 to facilitate stable data capture.

Figure 11D:
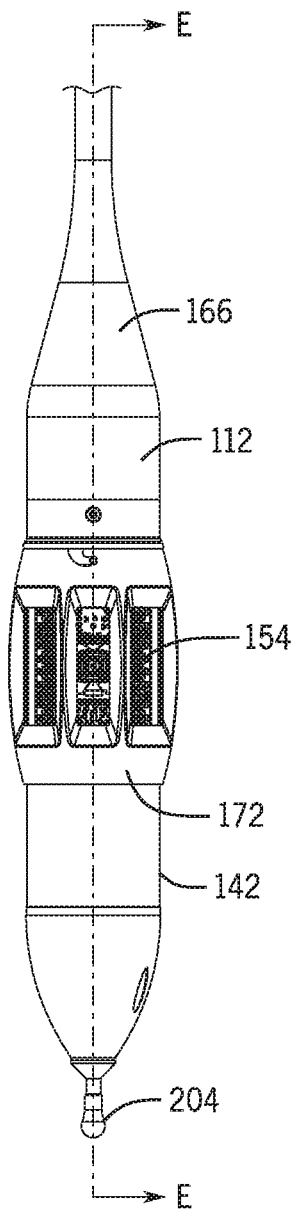
FIG. 11D is a side elevational view of the elongate probe.
Figure 11E:
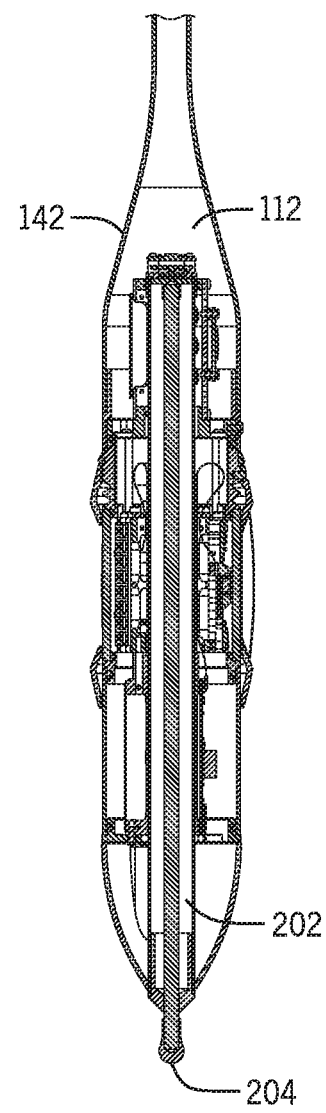
FIG. 11E is a cross-sectional view of the elongate probe taken along the line E-E in FIG. 11D.
Figure 13:
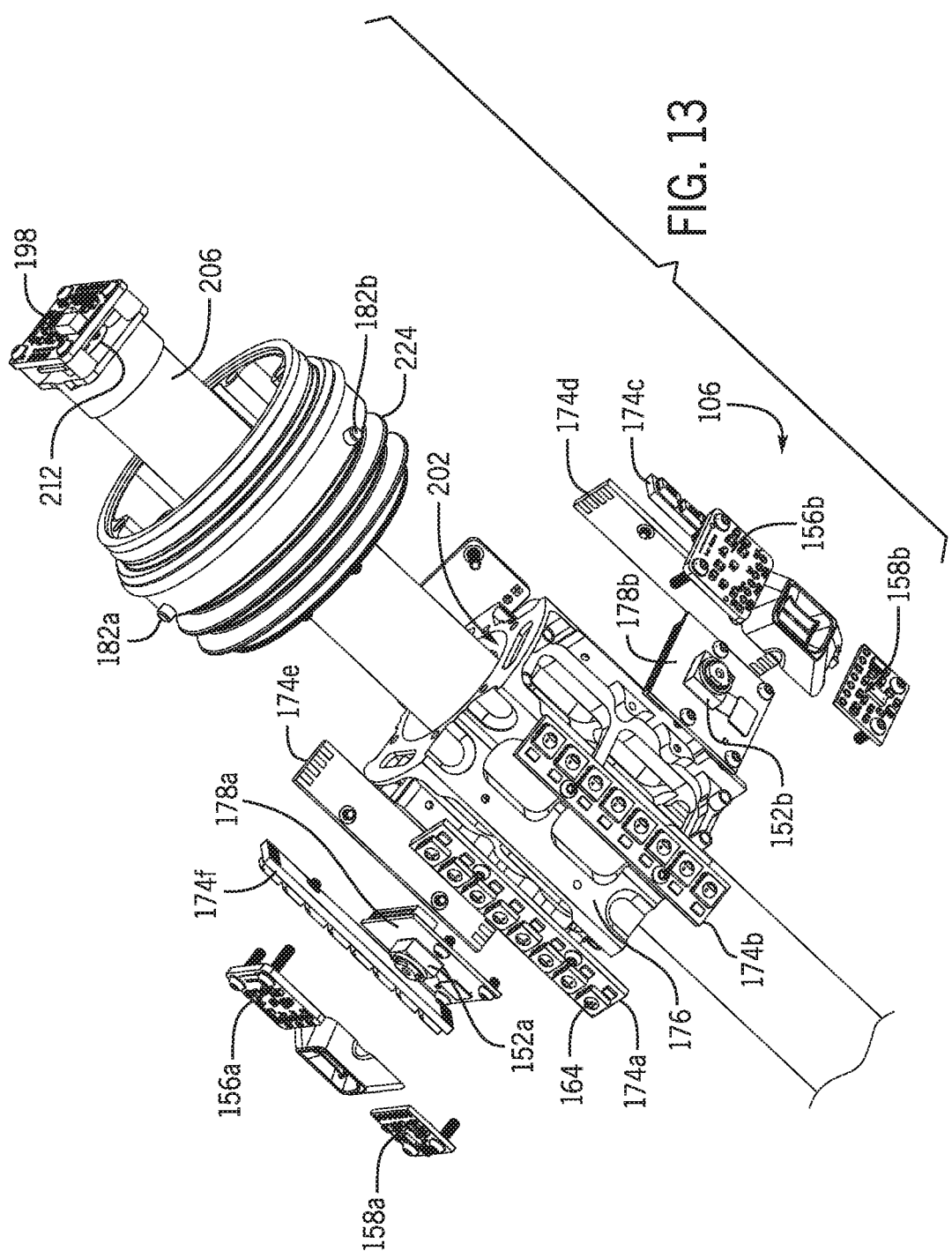
FIG. 13 is a partial, enlarged, exploded view of the elongate probe of FIGS. 12A and 12B.
Figure 14:
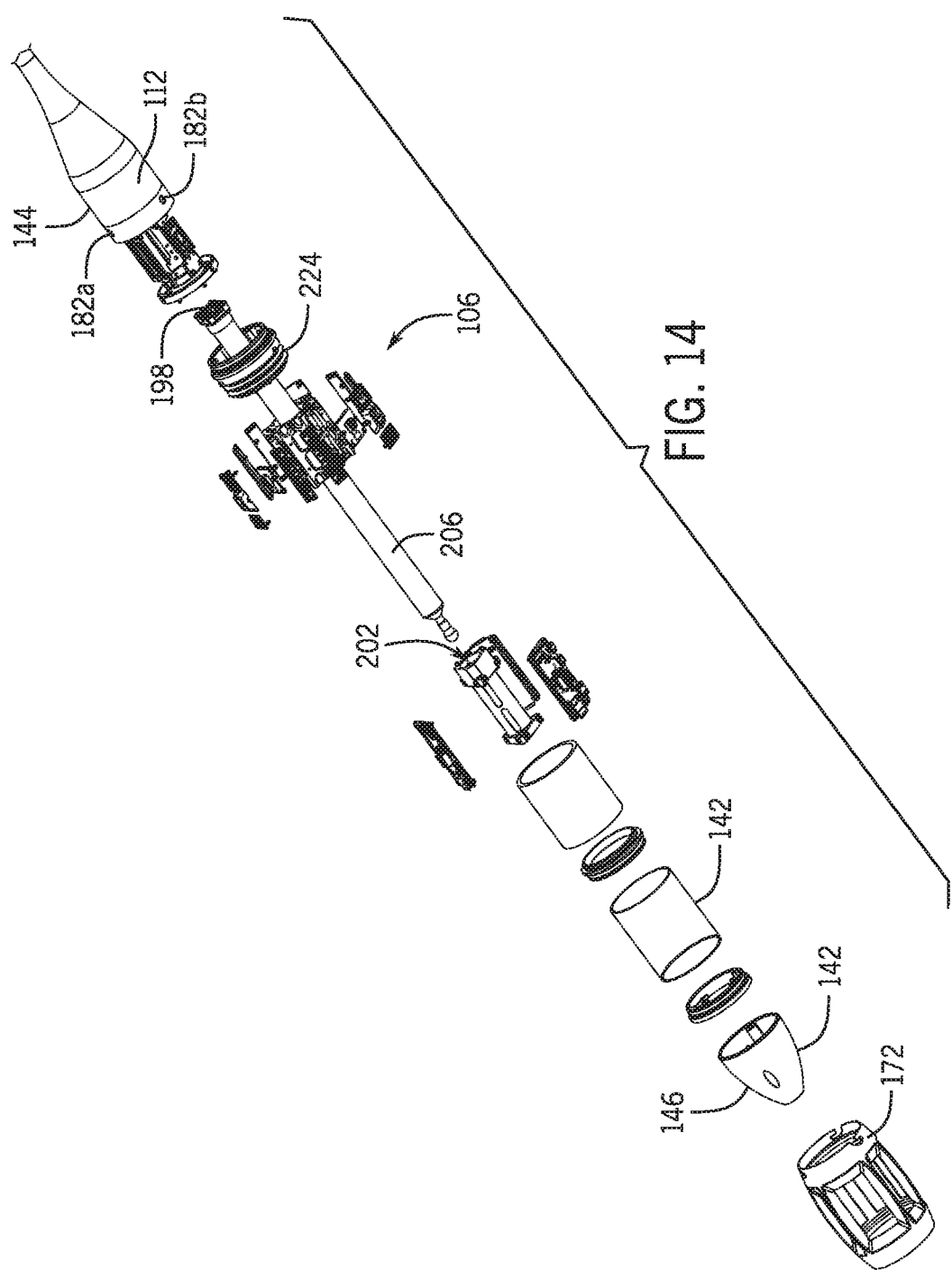
FIG. 14 is an enlarged, exploded view of the elongate probe.

Referring again to FIGS. 11D, 13, and 14 the elongate probe 112 and sensor package 106 have an interior space or lumen 202 disposed centrally therein. A ground contact probe 204, depicted in FIGS. 21-24 is further disposed within the lumen 202, as illustrated by FIGS. 11F, 11E, and 25. Referring back to FIGS. 21-24, the ground contact probe 204 comprises a tube 206 with a rod 208 disposed through the hollow interior of the tube 206. When an exterior end 210 of the rod 208 contacts the ground, the rod 208 slides vertically within the internal tube 206. A ground probe LiDAR sensor 212 or other linear sensor configured at an upper end 214 of the tube 206 monitors a position of the rod 206 by detecting an interior end 216 thereof within the tube 206. In this manner, a distance the rod 208 has moved is observed. A downward facing LiDAR sensor may produce inaccurate observations of distance to the ground resulting from detection of leaves, spider webs, and/or other debris within and below the crop canopy. However, the physical rod 208 has enough weight and structural integrity to negotiate small obstructions so that a reliable ground observation or solid object detection is obtained. Observations made by the ground contact probe 204 may be filtered by software algorithms, which may be performed by the microprocessor/controller 114, to smooth the data for correspondingly smooth lowering of the UAS 108 to a desired depth. The weight and length of the ground touch sensor rod 208 may be customized to suit different crops and/or crop conditions.

Figure 21:
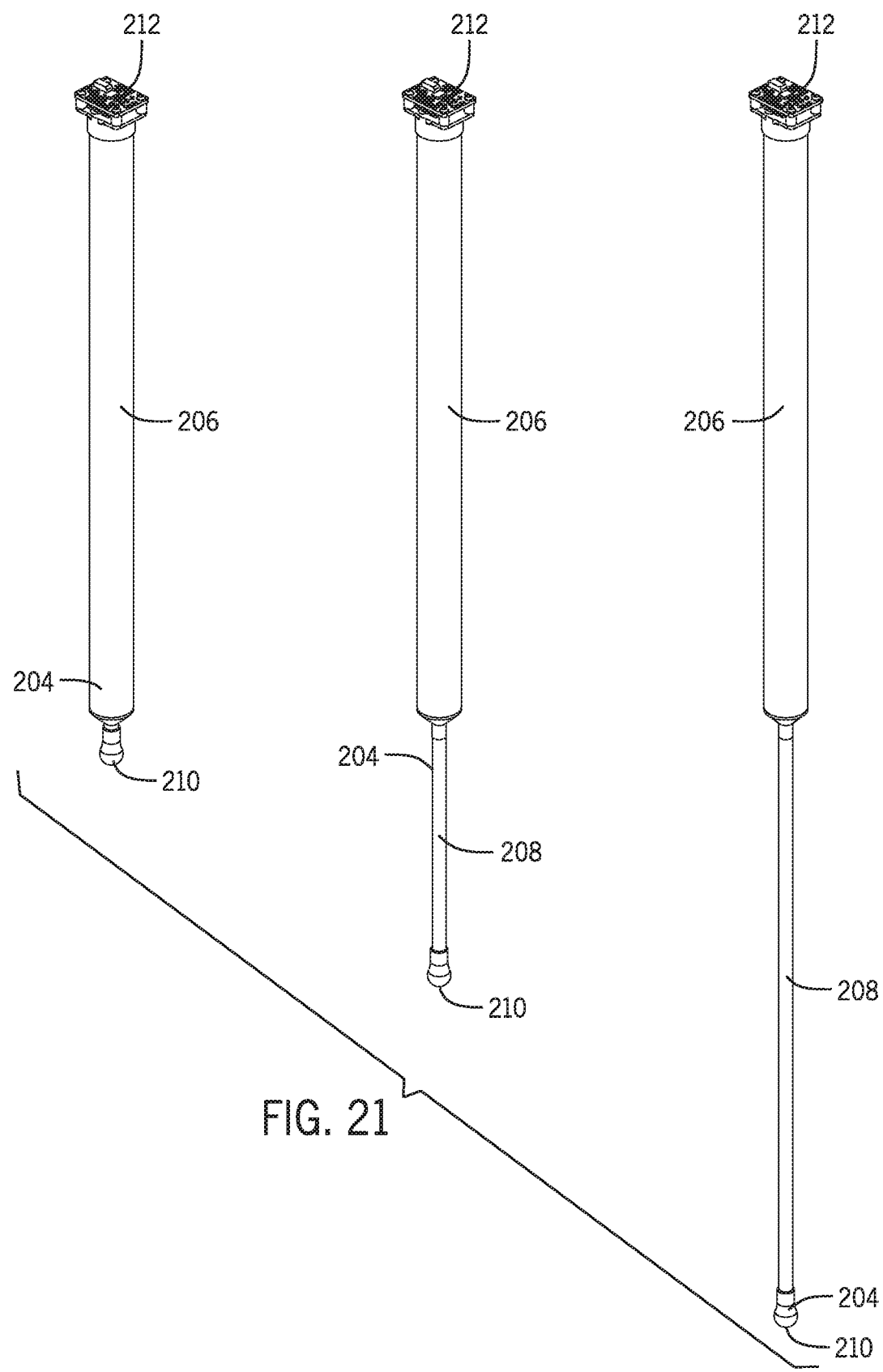
FIG. 21 is an isometric view from above of a ground contact probe in varying states of compression.
Figure 22B:
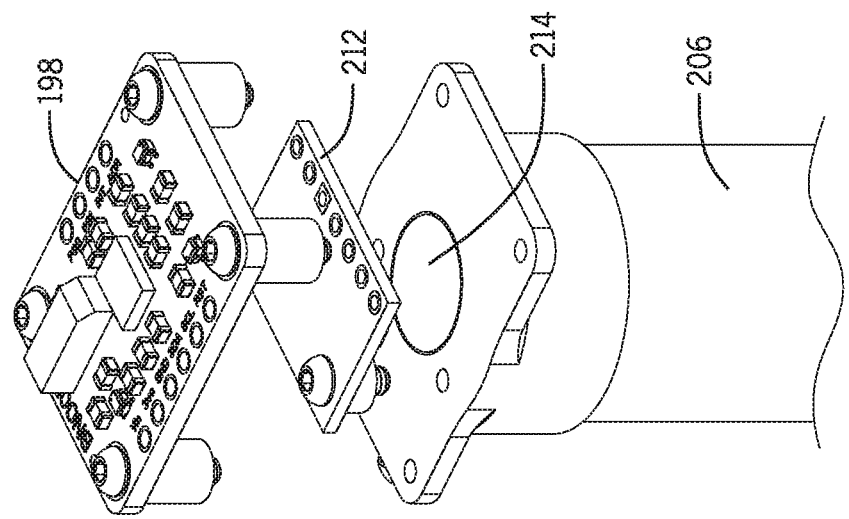
FIG. 22B is an exploded isometric view from above of the LiDAR sensor of FIG. 22A.
Figure 22A:
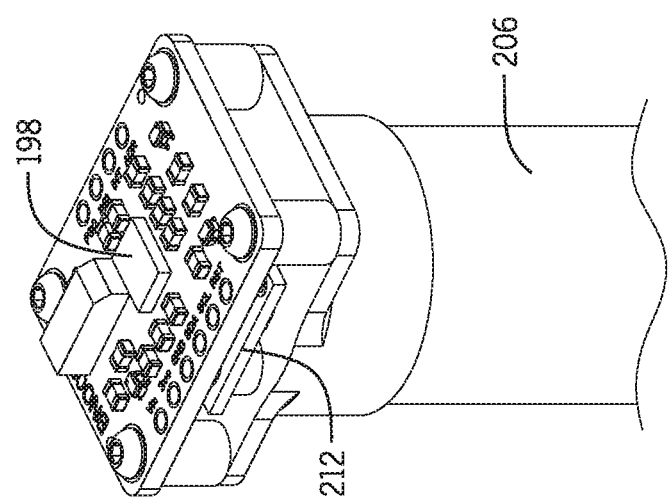
FIG. 22A is an enlarged isometric view from above of a LiDAR sensor on one end of a ground contact probe tube.

The reliable ground distance observations produced by the ground contact probe may be used by the controller 114 as a precautionary backup for the UAS navigation system. For circumstances when the downward facing microwave radar 162 is unable to detect a crop below, the ground contact probe 204 provides a fail-safe. The ground contact probe 204 may represent a "last chance" for the UAS 108 to increase altitude without grounding itself, i.e. "bail-out." Alternatively, in example embodiments, the ground contact probe 204 may provide precise low-to-ground altitude control for use in relatively short crops. A length of the rod 208 is predetermined and the ground probe LiDAR sensor 212 is arranged in vertical alignment with a mounting position of the rod 208, the ground contact probe 204 is capable of accurately determining the depth to which the elongate probe 112 is inserted into a short crop. FIG. 21 depicts the rod 208 at varying stages of compression from fully compressed on the left to fully extended on the right.

Data/observations captured by the sensor package 106 may be communicated to an internal storage device such as a SD card, USB thumb drive, solid-state hard drive, and/or transferred to the cloud using a cellular modem disposed within the housing assembly 184 shown in FIG. 6. This process may take place continuously during flight so that a data transfer step after landing is eliminated. The sensor package processor/controller 114 (FIG. 9A) may perform some processing of data before recording same to storage, or the data may be processed by remote microprocessor/computing device, such as one a server. Data such a temperature, pressure, humidity, longitude, and latitude, luminous flux readings, and/or other data may be written to image metatags of the images captured by the cameras 152a-c. Writing metatags to the captured images provides for easy portability to other software for easy creation of local, regional, national, and/or international georeferenced maps of observed crop stresses. Post-observation processing of data also shortens the time between data collection/observation and delivery of useful and easily digestible data to users/growers.

Following data capture and successful verification thereof, the sensor package processor/controller 114 instructs the UAS 108 to increase altitude, thereby withdrawing the retractable boom assembly 110 and sensor package 106 out of the crop canopy 102, as shown in FIG. 28. Upon reaching a predetermined altitude, the UAS 108 resumes navigation to the next field sampling point 218, repeats the "dipping" maneuver, and inserts the retractable boom assembly 110 into the crop canopy 102 for further data capture. As the UAS 108 navigates from point 218 to point 218, the multicolor sensor package LEDs 164 may be activated for use as a safety beacon, flashing intermittently to warn the local area that the system 100 is present. The LEDs 164 may also indicate, with one or more color coded pattern, the system status and/or result of diagnostic functions such as error detection, status of data transfer, etc. Following data capture at a final field sampling point 218 for a programmed mission, the UAS 108 automatically retracts the retractable boom assembly 110 and sensor package 106 to the first, rigid storage position 128 for an unassisted landing.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled. Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

INDUSTRIAL APPLICABILITY

The crop monitoring system, including the elongate probe and methods described herein, may provide a method of lowering operational costs compared to current labor-intensive scouting efforts by, instead, implementing autonomous scouting. Autonomous scouting may improve logistics and reduce emission of greenhouse gases from scouting vehicles. Further, autonomous scouting may facilitate better pesticide/fungicide/fertilizer spraying practices to reduce financial costs, support environmental stewardship, and enable compliance with present and future regulations related to controlled chemicals. Still further, autonomous scouting may positively impact farmer productivity, environmental stewardship, and crop protection management, thereby extending competitive advantages to the grower. Additional benefits of autonomous scouting include facilitation of better soil management practices based on accurate vegetation uptake of crop protection and fertility products, improved water use optimization based on improved zone management highlighting water deficiency, especially for irrigation plots, and improved food safety, quality, and sustainability. Also, grower associations (e.g., for corn, soybean, sugar beets, etc.) in the agriculture industry may create and maintain a database of regional pest infestation(s) and thereby accurately assess migration movements of pests for modeling and prevention tactics.

According to some embodiments of the presently disclosed crop monitoring system, the system components and methods described herein will provide farmers with an accurate picture of the field and crop conditions, such as in-field insect or disease pressure, stress with specific classification of cause, and degree of damage based on observed evidence. The system may also be used for documentation of other types of damage such as that caused by hail, wind, flood, or fire. Such an accurate representation of field and crop conditions may improve integrated pest management practices and optimization that increases yield while reducing pesticide use and human incursion into the ecosystem.

Many challenges exist in collecting data inside of a crop canopy with a UAS, including the following: navigating the UAS at a consistent safe altitude above multi types of crops in a stable enough manner to collect quality imagery and standardized data; creating a retractable boom assembly between the UAS and sensor package that allows for unencumbered penetration of the crop canopy without affecting the flight characteristics of the UAS or the normal UAS landing procedure; creating a micro-environment around the sensor package, while inside of the crop canopy, to properly position the probe to take an image and sensor readings that are agronomically consistent with what a trained agronomist would see if present at the sampling location. The disclosure hereinabove details a quick and affordable solution to these challenges.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled. Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. Preferred embodiments of this disclosure are described herein, including the best mode known to the inventors for carrying out the disclosure. It should be understood that the illustrated embodiments are exemplary only, and should not be taken as limiting the scope of the disclosure.

We claim:

1. A system for monitoring crop conditions below a crop canopy, the monitoring system comprising:
   an unmanned aerial vehicle having a retractable boom assembly and a first inertial measurement unit;
   an elongate probe coupled to the retractable boom assembly, the elongate probe including a sensor package and a second inertial measurement unit;
   a controller coupled to the unmanned aerial vehicle, wherein the controller, the first inertial measurement unit, and the second inertial measurement unit operate together to:
   (i) position the elongate probe between a ground surface in which the crops are planted and an upper level of a crop canopy for collection of crop data by the sensor package; and
   (ii) adjust navigation of the unmanned aerial vehicle according to forces developed by in-flight movement of the retractable boom assembly and the elongate probe.

2. The system of claim 1, wherein the retractable boom assembly further comprises:
   an actuator;
   a plurality of arms, wherein the actuator operates on one of the plurality of arms;
   a plurality of flexible hinges; and
   wherein in response to actuation the plurality of arms operate together to flex at the flexible hinges and retract the retractable boom assembly to a tucked position beneath the unmanned aerial vehicle.

3. The system of claim 1, wherein the controller micro-positions the unmanned aerial vehicle in response to observations from the sensor package, wherein the micro-positioning improves one or more parameters of the sensor package observations.

4. The system of claim 3, wherein the sensor package includes a sensor with a sensor frame, and wherein improving one or more parameters of the sensor package observation includes moving a target closer to a center of the sensor frame.

5. The system of claim 1, the sensor package further comprising:
   a ground touch probe operably connected to the unmanned aerial vehicle,
   wherein navigation of the unmanned aerial vehicle is adjusted in response to the ground touch probe contacting ground.

6. The system of claim 1, wherein the sensor package further comprises one or more of: at least one camera, at least one LiDAR sensor, and at least one luminous flux sensor.

7. The system of claim 6, wherein the sensor package further includes environmental sensors and three cameras that are positioned approximately 120 degrees from one another.

8. The system of claim 1, wherein the retractable boom assembly has a retracted position and an extended position;
wherein the retractable boom assembly moves from the retracted position to the extended position to dispose the elongate probe distal from the unmanned aerial vehicle; and
wherein the unmanned aerial vehicle maneuvers the elongate probe below the crop canopy while the retractable boom assembly is in the extended position.

9. The system of claim 1, further comprising a downward facing sensor operably coupled to the unmanned aerial vehicle and configured to determine the upper level of the crop canopy, and
wherein the controller utilizes one or more observations from the downward facing sensor to adjust an altitude of the unmanned aerial vehicle in order to position the elongate probe between the ground surface and the upper level of the crop canopy.

10. The system of claim 1, further comprising a downward facing sensor operably coupled to the unmanned aerial vehicle and configured to determine the upper level of the crop canopy, and wherein the controller utilizes one or more observations from the downward facing sensor to retract or extend the retractable boom assembly in order to position the elongate probe between the ground surface and the upper level of the crop canopy.

11. The system of claim 1, wherein the sensor package further includes a sensor that is (i) positioned radially outward from the elongate probe, and (ii) configured to aid in determining whether the elongate probe is positioned between the ground surface and the upper level of the crop canopy.

12. The system of claim 1, further comprising a memory unit that is operably coupled to the unmanned aerial vehicle, said memory being configured to store a crop data collection pattern that is based on a Normalized Difference Vegetative Index.

13. The system of claim 1 wherein the unmanned aerial vehicle has rotor arms that include propellers, and wherein a length of the retractable boom assembly and a length of the rotor arms function together to reduce a downwardly directed force created by the propellers and applied to the elongate probe.

14. The system of claim 1, wherein an extent of the flight path of the unmanned aerial vehicle is determined by the controller without human intervention.

15. A system for aerial monitoring of crops, the system comprising:
an unmanned aerial vehicle (UAV) having:
first inertial measurement unit and a downward facing sensor operably coupled to the UAV, wherein the downward facing sensor is configured to determine an upper level of a crop canopy;
an elongate probe with a sensor package and a second inertial measurement unit;
retraction mechanism to operably couple the elongate probe to the UAV;
wherein the retraction mechanism is configured to retract the elongate probe into close proximity to the UAV during launch and landing of the UAV;
wherein the observations from the downward facing sensor, first inertial measurement, second inertial measurement, and the retraction mechanism are utilized to:
(i) deploy the elongate probe away from the UAV during flight such that the elongate probe is positioned in a space below the upper level of the crop canopy and above a ground surface in which the crops are located in order to collect crop data; and
(ii) reposition the UAV according to forces developed by in-flight movement of the retraction mechanism and the elongate probe.

16. The system of claim 15, further comprising a controller that is operably coupled to the UAV, said controller is configured to micro-position the UAV in response to the one or more observations of the sensor package.

17. The system of claim 16, wherein the sensor package includes a sensor with a sensor frame, and wherein said micro-positioning is configured to move a target closer to a center of the sensor frame.

18. The system of claim 11, further comprising a compressible ground touch probe disposed within the elongate probe;
wherein one or more observations of the ground touch probe, acquired in real time, results in a controller micro-positioning the UAV to maintain the sensor package at a consistent height relative to the crop canopy.

19. The system of claim 15, wherein the retraction mechanism comprises at least one of the following: (i) a boom assembly, (ii) a reel and cable, and (iii) a combination of a boom assembly and a cable.

20. The system of claim 15, further comprising a controller that is coupled to the UAV, said controller utilizes one or more observations from the downward facing sensor to adjust an altitude of the UAV in order to position the elongate probe between the ground surface and the upper level of the crop canopy.

21. The system of claim 15, wherein the sensor package further includes a sensor that is (i) positioned radially outward from the elongate probe, and (ii) configured to aid in determining whether the elongate probe is positioned between the ground surface and the upper level of the crop canopy.

22. The system of claim 15, further comprising a memory unit that is operably coupled to the UAV, wherein an extent of the flight path of the UAV is autonomous and is based on a crop data collection pattern that is stored within the memory unit.

23. The system of claim 15, wherein the sensor package includes:
three cameras that are positioned approximately 120 degrees from one another; and
at least three pairs of light emitting diodes, wherein each pair of the light emitting diodes is positioned between each pair of cameras.

24. The system of claim 15, wherein the UAV has rotor arms that include propellers, and wherein a length of the retraction mechanism and a length of the rotor arms function together to reduce a downwardly directed force created by the propellers and applied to the elongate probe.

* * * * *